United States Patent
Huh et al.

(10) Patent No.: US 11,759,364 B2
(45) Date of Patent: Sep. 19, 2023

(54) PROTECTOR FOR WELDING

(71) Applicant: OTOS WING.CO., LTD., Seoul (KR)

(72) Inventors: Moon Young Huh, Seoul (KR); Sung Won Huh, Seoul (KR)

(73) Assignee: OTOS WING.CO., LTD., Seoul (KR)

( * ) Notice: Subject to any disclaimer, the term of this patent is extended or adjusted under 35 U.S.C. 154(b) by 104 days.

(21) Appl. No.: 17/186,584

(22) Filed: Feb. 26, 2021

(65) Prior Publication Data

US 2021/0267804 A1    Sep. 2, 2021

(30) Foreign Application Priority Data

Feb. 27, 2020    (KR) ..................... 10-2020-0024552

(51) Int. Cl.
*A61F 9/06* (2006.01)
(52) U.S. Cl.
CPC ..................... *A61F 9/06* (2013.01)
(58) Field of Classification Search
CPC .. A61F 9/06; A61F 9/061; A61F 9/062; A61F 9/064; A61F 9/065; A61F 9/067; A61F 9/068; B23K 9/322; A41D 2600/202
USPC ................. 2/8.1, 8.2, 8.3
See application file for complete search history.

(56) References Cited

U.S. PATENT DOCUMENTS

| | | | | |
|---|---|---|---|---|
| 1,399,602 A | * | 12/1921 | Mengle ..................... | A61F 9/06 2/8.2 |
| 1,601,830 A | * | 10/1926 | Huntsman ................. | A61F 9/06 2/8.2 |
| 1,885,426 A | * | 11/1932 | Flood ........................ | A61F 9/06 2/8.2 |
| 2,045,802 A | * | 6/1936 | Richter ..................... | A61F 9/06 340/815.73 |
| 2,277,090 A | * | 3/1942 | Feiler ...................... | A61F 9/025 33/203.11 |
| 2,410,256 A | * | 10/1946 | Anderson ............... | A61F 9/061 D29/110 |
| 2,469,810 A | * | 5/1949 | Charles ..................... | A61F 9/06 2/8.1 |
| 2,817,087 A | * | 12/1957 | Rush ........................ | A61F 9/06 2/8.1 |

(Continued)

FOREIGN PATENT DOCUMENTS

GB    442187 A  *  2/1936  ............... A61F 9/06
GB    1154740       6/1969

(Continued)

OTHER PUBLICATIONS

Office Action dated Oct. 26, 2021 in German Application No. 10 2021 104 728.5.

(Continued)

*Primary Examiner* — Khoa D Huynh
*Assistant Examiner* — Grace Huang
(74) *Attorney, Agent, or Firm* — Knobbe, Martens, Olson & Bear, LLP

(57) ABSTRACT

This application relates to a protector for welding. In one aspect, the protector includes a main body configured to protect a face of a welder and a darkening section located on a front surface portion of the main body. The protector may also include an auxiliary shield that is arranged adjacent to one edge of a main body and includes a main surface portion extending in a direction away from the main body.

7 Claims, 22 Drawing Sheets

(56) References Cited

U.S. PATENT DOCUMENTS

| | | | | |
|---|---|---|---|---|
| 3,026,525 | A * | 3/1962 | Gyorfy | A42B 3/322 |
| | | | | 2/202 |
| 3,768,099 | A * | 10/1973 | Manz | A61F 9/061 |
| | | | | 359/889 |
| 3,868,727 | A * | 3/1975 | Paschall | A61F 9/064 |
| | | | | 2/12 |
| 4,986,282 | A * | 1/1991 | Stackhouse | A61F 9/02 |
| | | | | 128/857 |
| 5,224,219 | A * | 7/1993 | Edwards | A61F 9/061 |
| | | | | 2/8.3 |
| 6,151,711 | A * | 11/2000 | Edwards | A61F 9/061 |
| | | | | 2/8.3 |
| 6,185,739 | B1 | 2/2001 | Verkic et al. | |
| 8,381,312 | B2 * | 2/2013 | Seo | A61F 9/064 |
| | | | | 2/8.4 |
| 8,721,103 | B2 * | 5/2014 | Robinson | H05B 47/105 |
| | | | | 362/276 |
| 10,278,867 | B2 * | 5/2019 | Watkins | A61F 9/064 |
| 2004/0117888 | A1 * | 6/2004 | Wang-Lee | A42B 3/20 |
| | | | | 2/9 |
| 2010/0212058 | A1 * | 8/2010 | Wanhainen | A42B 3/225 |
| | | | | 2/424 |
| 2015/0359677 | A1 * | 12/2015 | Sommers | A42B 3/225 |
| | | | | 2/8.2 |

FOREIGN PATENT DOCUMENTS

| | | |
|---|---|---|
| KR | 20-1994-0012068 U | 6/1994 |
| KR | 10-0767702 B1 | 10/2007 |
| KR | 10-2009-0095179 A | 9/2009 |

OTHER PUBLICATIONS

Office Action dated Oct. 15, 2021 in Korean Application No. 10-2020-0024552.

* cited by examiner

PROTECTOR FOR WELDING

CROSS-REFERENCE TO RELATED APPLICATIONS

The present application claims priority under 35 U.S.C. 119(a) to Korean Patent Application No. 10-2020-0024552, filed on Feb. 27, 2020, which is incorporated herein by reference in its entirety.

BACKGROUND

Technical Field

Embodiments of the present disclosure relate to a protector for welding.

Description of Related Technology

A welder wears a protective device to protect from light and high heat generated during a welding process such as arc welding. The protective device is very diverse in shape and structure, such as a shape that covers the eyes of the welder or a shape that covers the head of the welder depending on the work of the welder.

SUMMARY

Embodiments of the present disclosure provide a protector for welding capable of at least partially protecting the body of a welder and has excellent storage capability and mobility. However, the problems are exemplary and do not limit the scope of the present disclosure.

An embodiment of the present disclosure provides a protector for welding including a main body configured to protect a face of a welder, a darkening section located on a front surface portion of the main body, and an main body that is arranged adjacent to one edge of a face shield and includes a main surface portion extending in a direction away from the main body.

The auxiliary shield may include at least one selected from metal or plastic.

The auxiliary shield may be linearly movable on the main body.

One of the main body and the auxiliary shield may include a recess, and the other may include a protrusion coupled to the recess, and the recess may have a first length which is greater than a first width of the recess and extends in a first direction.

Any one of the auxiliary shield and the main body may include a protrusion, and the other may include a hole coupled to the protrusion.

One end of the auxiliary shield may overlap a portion including the one edge of the main body through a coupling structure of the protrusion and the hole.

Any one of the auxiliary shield and the main body may be rotationally movable with respect to the other one of the auxiliary shield and the main body by a protrusion which is coupled to the hole and rotates around an axis penetrating the protrusion.

The auxiliary shield may be rotationally movable between a first state and a second state according to rotation of the protrusion, and the first state may be a state in which an overlapping area of the auxiliary shield and the main body is relatively large, and the second state may be a state in which the overlapping area of the auxiliary shield and the main body is relatively small.

The auxiliary shield may be fitted to the one edge of the main body.

Any one of the main body and the auxiliary shield may include a recess, and the other one may include a protrusion coupled to the recess, and an outer width of the recess may be smaller than an inner width of the recess.

Other aspects, characteristics, and advantages in addition to the above description will become apparent from the following drawings, claims, and detailed description of the disclosure.

Embodiments of the present disclosure may provide a protective device including an auxiliary shield that improves ease of operation and wearing, storage capability, mobility, and so on. The above-described effects are exemplary, and effects according to the embodiments will be described in detail through the following description.

BRIEF DESCRIPTION OF THE DRAWINGS

Various embodiments of the present disclosure will become more apparent in view of the attached drawings and accompanying detailed description.

DETAILED DESCRIPTION

Figure 1:
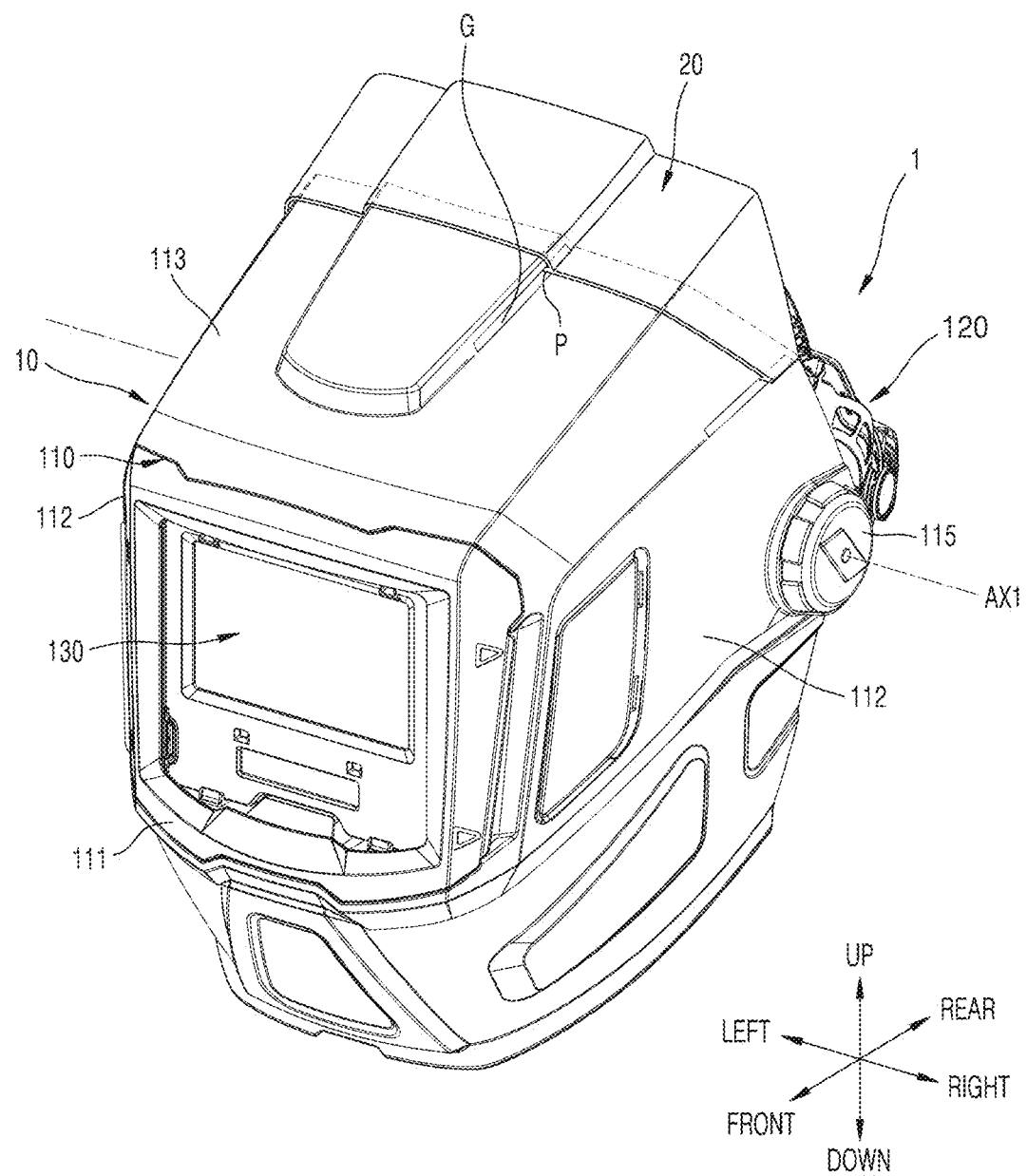
FIG. 1 is a perspective view schematically illustrating a protector for welding according to an embodiment of the present disclosure.

A protective device may include various components for protecting various parts of the body of a welder, and it is difficult to store the protective device including the various components.

Since the present disclosure may be variously modified and have various embodiments, specific embodiments will be illustrated in the drawings and described in detail in the detailed description. Effects and characteristics of the present disclosure, and a method of achieving the effects and characteristics will be apparent with reference to the embodiments to be described below in detail together with the drawings. However, the present disclosure is not limited to the embodiments to be disclosed below and may be implemented in various forms.

In the following embodiments, terms such as first and second are used for the purpose of distinguishing one configuration element from other configuration elements rather than a restrictive meaning.

In the following embodiments, a singular expression includes a plural expression unless the context dearly indicates otherwise.

In the following embodiments, terms such as include or have means that characteristics or configuration elements described in the specification are present, and do not preclude a possibility of adding one or more other characteristics or configuration elements.

In the following embodiments, when it is described that a portion such as a region or a configuration element is on or over another portion, this includes not only a case in which the region or the configuration element is directly above another portion, but also a case in which another region, another configuration element, or so on is placed therebetween.

In the drawings, configuration elements may be exaggerated or reduced in size for the sake of convenient description. For example, a size and a thickness of each configuration element illustrated in the drawings are randomly illustrated for the sake of convenient description, and thus, the present disclosure is not limited to what is illustrated.

When a certain embodiment may be implemented differently, a specific process order may be performed differently from the described order. For example, two processes described in succession may be performed substantially simultaneously or may be performed in an order opposite to the described order.

In the following embodiments, when it is described that a region, a configuration element, or so on is connected, this includes not only a case in which the region or the configuration element is directly connected, but also a case in which another region or configuration element is placed therebetween to be indirectly connected.

Figure 2:
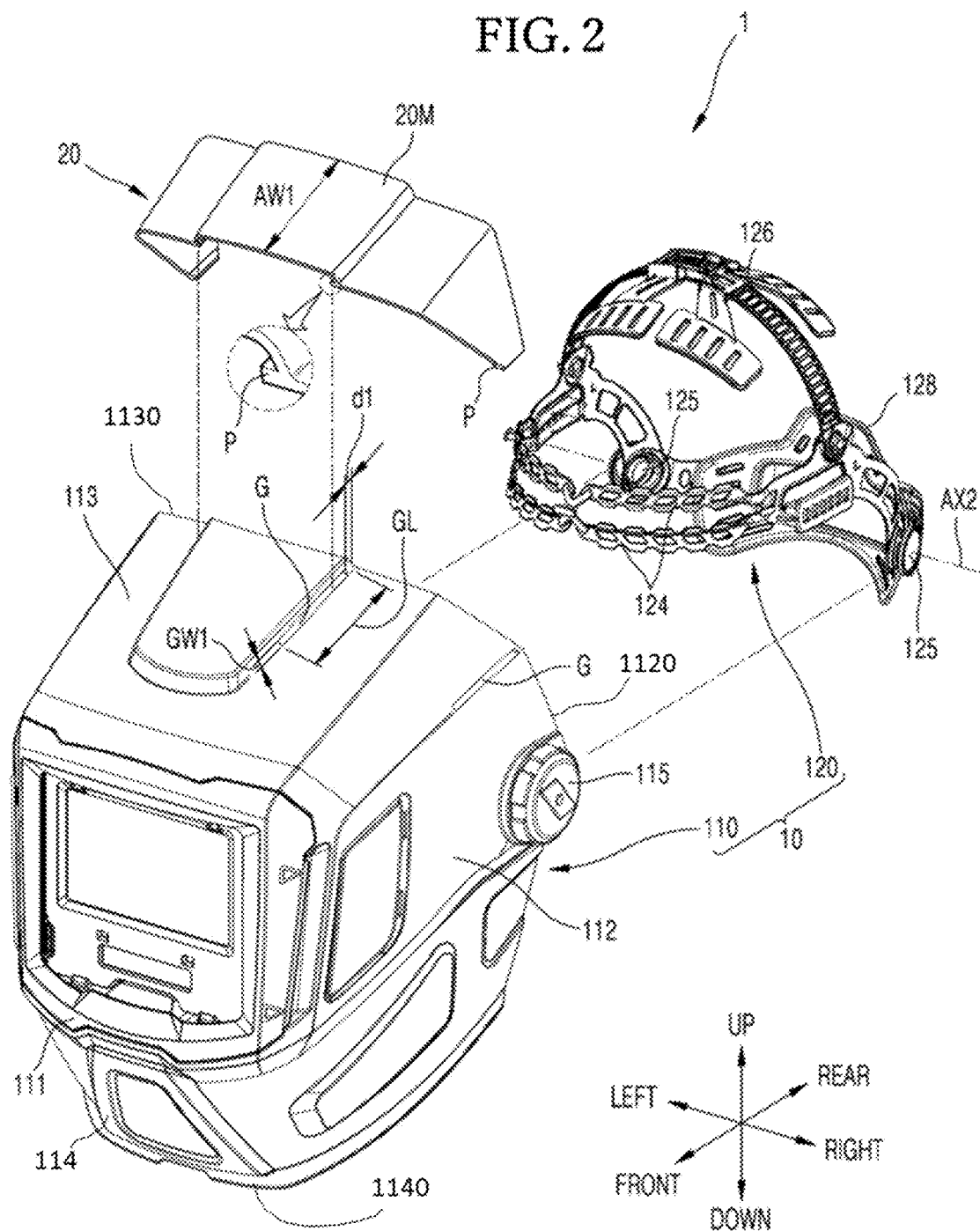
FIG. 2 is an exploded perspective view of FIG. 1.

FIG. 1 is a perspective view schematically illustrating a protector for welding according to an embodiment of the present disclosure, FIG. 2 is an exploded perspective view of FIG. 1, FIGS. 3A-3C are perspective views illustrating part of the protector for welding and illustrates part of a face shield and an auxiliary shield.

Referring to FIGS. 1 and 2, a protector for welding 1 includes a face shield 10 that protects a face of a welder and an auxiliary shield 20 that covers other parts of a body of the welder that the face shield 10 cannot cover.

The face shield 10 may protect at least part of the face of the welder. The face shield 10 may include a main body 110 and a wearing portion 120 that fixes the main body 110 to a head of the welder.

The main body 110 may include a hard material with a predetermined strength. The main body 110 may include one or more of metal or plastic. In one embodiment, the main body 110 may include an element such as a spark that may occur during welding and/or a material that is resistant to external impact. In one embodiment, the main body 110 may include heat-resistant plastic and/or reinforced plastic. The material of the main body 110 described above is distinguished from a material that does not maintain a shape, such as a fabric (for example, flame retardant cloth), and may maintain the shape unless a separate external force is applied.

The main body 110 may include a pair of first pivot portions 115 arranged on both sides. The first pivot portions 115 may provide an axis around which the main body 110 may rotate. For example, the main body 110 may vertically rotate around an axis AX1 penetrating the pair of first pivot portions 115, and the main body 110 may cover or may not cover the face of a welder according to the rotation of the main body 110. For example, during operation, the main body 110 may cover the face of the welder, and when the operation is not performed, the main body 110 may rotate around the axis AX1 penetrating the first pivot unit 115 to be placed on an upper portion of the head of the welder.

The main body 110 of the face shield 10 may include a main surface portion that covers the face of a user including the eyes, nose, and/or mouth of the welder. The main surface portion may include a front surface portion 111 corresponding to the eyes, nose, or/and mouth, side surface portions 112 that is bent from the front surface portion 111 and is arranged on the left and right sides of the front surface portion 111, and an upper surface portion 113 that is bent from the front surface portion 111 and is arranged above the front portion 111. The main surface portion includes a bottom portion 114 disposed below the first surface portion 111 and inclined inwardly toward the face of the welder with respect to the front surface portion 111. In one embodiment illustrated in FIG. 2, the upper surface portion 113 includes a first rear edge 1130, each side surface portion 112 includes a second rear edge 1120, and the bottom portion 114 includes a bottom edge 1140.

The side portions 112 and the upper surface portion 113 may each be bent from the front portion 111 and may extend in a direction away from the front surface portion 111, and thus, the three-dimensional face of the welder may be three-dimensionally protected by the main surface portion of the main body 110.

The wearing portion 120 is an element that couples the protector for welding to the head of the welder, and the wearing portion 120 may be a headgear type strap as illustrated in FIGS. 1 and 2. In one embodiment, the wearing portion 120 may include a first support portion 124 extending to include a portion located on the forehead of the welder, a second support portion 126 extending upwards the head of the welder, and a third support portion 128 extending to be located on a back portion of the head of the welder. The wearing portion 120 may include a lever for adjusting a size of the wearing portion 120. The third support portion 128 may include a cushion material for feeling of wearing.

A pair of second pivot portions 125 may be arranged between the first support portion 124 and the third support portion 128. The pair of second pivot portions 125 may provide an axis AX2 around which the third support portion 128 may rotate with respect to the first support portion 124. For example, the third support portion 128 may rotate relatively with respect to the first support portion 124, around the axis AX2 penetrating the pair of second pivot portions 125. The second pivot portions 125 may be located on a different axis from the first pivot portions 115 or may be located on the same axis as the first pivot portions 115. For example, the axis AX2 penetrating the second pivot portions 125 may be located on the same axis as the axis AX1 penetrating the first pivot portions 115 or may be located on different axis lines.

FIGS. 1 and 2 illustrate a case in which the wearing portion 120 is a headgear type strap, and the wearing portion 120 may be formed of an elastic material and may be a band-type strap with an adjustable length as another embodiment.

A darkening section 130 may be exposed to the outside through an opening formed in part of the main body 110, for example, the front surface portion 111 and may be arranged to correspond to the eyes of a welder. The darkening section 130 may include a light blocking filter. The light blocking filter may include a liquid crystal, and a degree of blackening of the darkening section 130 may be adjusted according to an alignment direction of the liquid crystal. The darkening section 130 may include an automatic light blocking filter. The automatic light blocking filter may adjust the degree of blackening based on light sensing information from a sensor provided around the darkening section 130.

The auxiliary shield 20 may protect the body of a welder that is not covered by the main body 110 of the face shield 10, for example, an upper side of the head, ears, and/or neck of the welder. The auxiliary shield 20 may be arranged on one or more sides selected from the front surface portion 111, the side surface portions 112, and the upper surface portion 113 of the main body 110. In this regard, FIGS. 1 and 2 illustrate an embodiment in which the auxiliary shield 20 is arranged adjacent to the upper surface portion 113 of the main body 110 so as to cover an upper side of the head of the welder.

The auxiliary shield 20 may be formed of a hard material. The auxiliary shield 20 may include one or more of metal or plastic. In one embodiment, the auxiliary shield 20 may include a material that is resistant to heat and/or external impact which may occur during welding. For example, the auxiliary shield 20 may include heat-resistant plastic and/or reinforced plastic. The auxiliary shield 20 may include the same material as the main body 110 or may include a material different from the main body 110.

The auxiliary shield 20 may extend in a direction away from one edge of the main body 110. For example, as illustrated in FIGS. 1 and 2, the auxiliary shield 20 may extend in a direction away from the upper surface portion 113 of the main body 110. A main surface portion 20M of the auxiliary shield 20 may have a predetermined area for covering part of the head of the welder that the main body 110 does not cover. Since the auxiliary shield 20 has a predetermined thickness, the auxiliary shield 20 may include the main surface portion 20M and a side surface in a thickness direction perpendicular to the main surface portion 20M. The main surface portion 20M of the auxiliary shield 20 is an element that is distinguished from a side surface portion having a very small area and covers part of the head of the welder. A width AW1 of the auxiliary shield 20, for example, a width of the main surface portion 20M may range from approximately 1 cm to approximately 10 cm. In some embodiments, the width AW1 of the auxiliary shield 20 may be approximately 1 cm to approximately 7 cm, or approximately 1 cm to approximately 5 cm.

The auxiliary shield 20 may be coupled to the main body 110. One of the main body 110 and the auxiliary shield 20 may include a protrusion and the other may include a groove (or recess). The main surface portion of the main body 110, for example, as illustrated in FIGS. 1, 2, and 3A, grooves G may be formed in the upper surface portion 113, and the auxiliary shield 20 may be provided with protrusions P, and the protrusions P may be inserted into the grooves G as illustrated in FIGS. 3B and 3C.

Figure 3A:
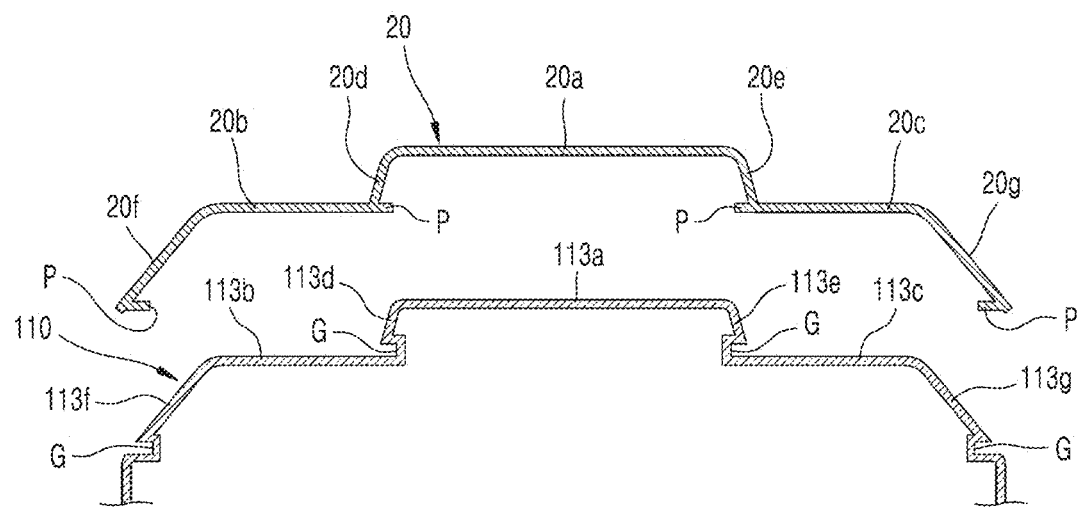
FIGS. 3A-3C are perspective views illustrating part of a protector for welding and illustrates part of a face shield and part of an auxiliary shield.
Figure 3B:
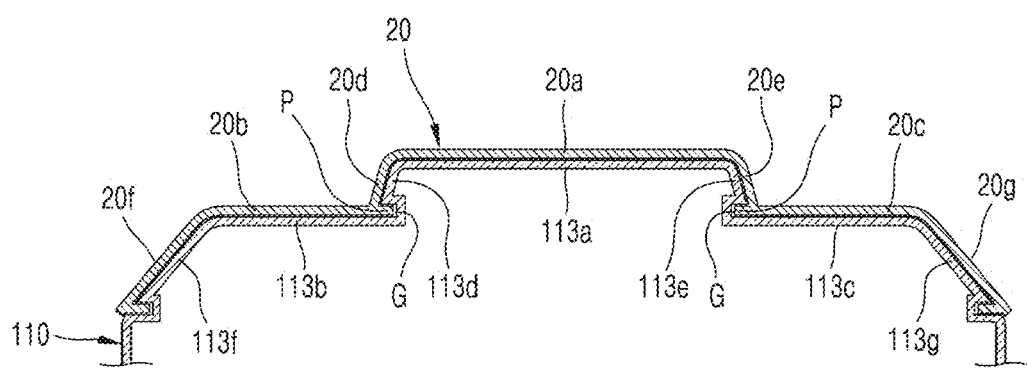
Figure 3C:
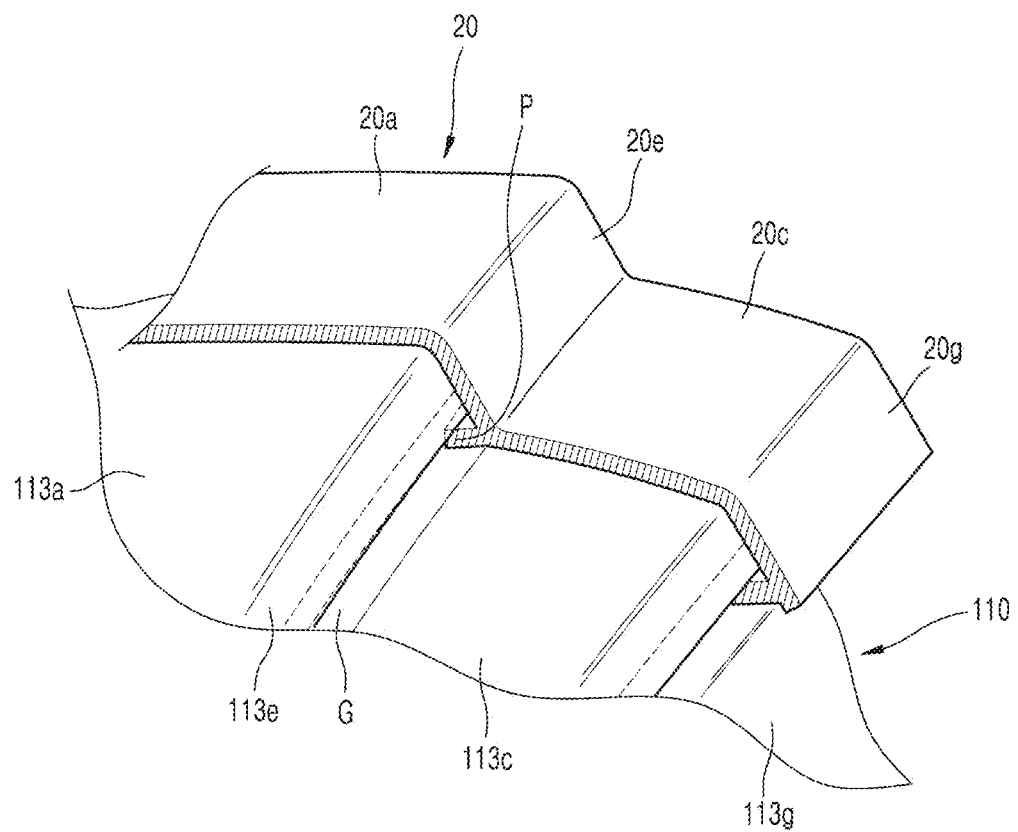

The upper surface portion 113 of the main body 110 may include a plurality of sub-surface portions, and for example, the upper surface portion 113 may include a first sub-surface portion 113a, and a second sub-surface portion 113b and a third sub-surface portion 113c which are arranged on both sides of the first sub-surface portion 113a as illustrated in FIG. 3A. The first sub-surface portion 113a is located on a different surface from the second sub-surface portion 113b and the third sub-surface portion 113c, and makes a step difference with the second sub-surface portion 113b and the third sub-surface portion 113c, and a fourth sub-surface portion 113d connects the first sub-surface portion 113a and the second sub-surface portion 113b to each other in a state of being located therebetween, and a fifth sub-surface portion 113e connects the first sub-surface portion 113a and the third sub-surface portion 113c to each other in a state of being located therebetween. For example, the grooves G may be formed on the fourth sub-surface portion 113d and the fifth sub-surface portion 113e, respectively, which extend from both edges of the first sub-surface portion 113a and are bent with respect to the first sub-surface portion 113a.

Similarly, the grooves G each may be formed in the fifth sub-surface portion 113f which extends from one edge of the second sub-surface portion 113b and is bent from the second sub-surface portion 113b and may be formed in the sixth sub-surface portion 113g which extends from one edge of the third sub-surface portion 113c and is bent from the third sub-surface portion 113c. FIGS. 1 to 3C illustrate a structure in which four grooves G are formed, but the number of grooves G may be variously changed.

The grooves G may each extend in one direction, and the protrusions P of the auxiliary shield 20 may move in extending directions of the grooves G. For example, the grooves G may extend in directions in which the auxiliary shield 20 extends with respect to the main body 110 or/and directions away from the front surface portion 111 (for example, rear), and the protrusions P may move linearly in the extension directions and/or in the opposite directions in a state of being inserted into or coupled to the grooves G.

As the protrusions P of the auxiliary shield 20 move while being coupled to the grooves G, an overlapping area of the auxiliary shield 20 and the main body 110 may be variable. When it is necessary to further protect the head of a welder from heat, flames, or so on generated during welding, the auxiliary shield 20 may be moved in a direction away from the main body 110 (for example, rear), and the moved auxiliary shield 20 may cover a partial region of the head of the welder that is not covered by the main body 110. When welding is not performed, the auxiliary shield 20 may move toward the main body 110 (for example, forward), and the moved auxiliary shield 20 may increase the overlapping area with the main body 110. it is possible to increase efficiency of assembly such as easily storing the auxiliary shield 20 in a situation where welding is not required.

The groove G is spaced apart from the main body 110 with a first interval d1 between the groove G and the edge of the main body 110 as illustrated in FIG. 2. For example, a first interval d1 between an end of the groove G and the edge of the main body 110 may be at least 3 mm, or at least 5 mm, or at least 7 mm. In one embodiment, the first interval d1 may be 3 mm to 15 mm, or 3 mm to 10 mm. Since the groove G is spaced apart from the edge of the main body 110 with the first interval d1, it is possible to prevent the linearly moving protrusion P from being separated from the groove G, and when the auxiliary shield 20 moves, the groove G may function as a stopper.

The auxiliary shield 20 may have a shape corresponding to part of the main body 110 in which the auxiliary shield 20 is located. For example, the auxiliary shield 20 may have a shape corresponding to the upper surface portion 113, and as illustrated in FIG. 3A, the auxiliary shield 20 may include a plurality of portions. For example, the auxiliary shield 20 may include a first portion 20a, and a second portion 20b and a third portion 20c which are arranged on both sides of the first portion 20a. The first portion 20a may be located on a surface different from the second portion 20b and the third portion 20c and may form a step difference from the second portion 20b and the third portion 20c. A fourth portion 20d connecting the first portion 20a and the second portion 20b to each other may be located therebetween, and a fifth portion 20e connecting the first portion 20a and the third portion 20c to each other may be located therebetween. The first portion 20a, the second portion 20b, and the third portion 20c may correspond to the first sub-surface portion 113a, the second sub-surface portion 113b, and the third sub-surface portion 113c, respectively. The fourth portion 20d and the fifth portion 20e of the auxiliary shield 20 may correspond to the fourth sub-surface portion 113d and the fifth sub-surface portion 113e of the upper surface portion 113 of the main body 110, respectively, and the protrusions P may be provided in the fourth portion 20d and the fifth portion 20e, respectively, so as to correspond to the grooves G. For example, the protrusions P may be formed on the fourth portion 20d and the fifth portion 20e, respectively, which extends from both edges of the first portion 20a and are bent with respect to the first portion 20a. When the auxiliary shield 20 has a shape corresponding to part of the main body 110 in which the auxiliary shield 20 is located, an interval between the auxiliary shield 20 and the main body 110 may be reduced, and thus, welding spatter, fume, heat, and/or so on may be prevented from being transmitted to a user by the interval described above.

The protrusions P may be formed in the fourth portion 20d and the fifth portion 20e, respectively. In addition, the protrusions P each may be formed in the fifth portion 20f which extends from one edge of the second portion 20b and is bent with respect to the second portion 20b, and may be formed in the sixth portion 20g that extends from one edge of the third portion 20c and is bent with respect to the third portion 20c, FIGS. 1 to 3C illustrate a structure in which four grooves G and four protrusions P are formed, but the number of protrusions P may be variously changed as well as the number of grooves G.

FIGS. 1 to 3C illustrate that the grooves G are formed in the main body 110 and the protrusions P are provided in the auxiliary shield 20, but in another embodiment, the grooves G may be provided in the auxiliary shield, and the protrusions P may be formed in the main body 110.

Figure 4:
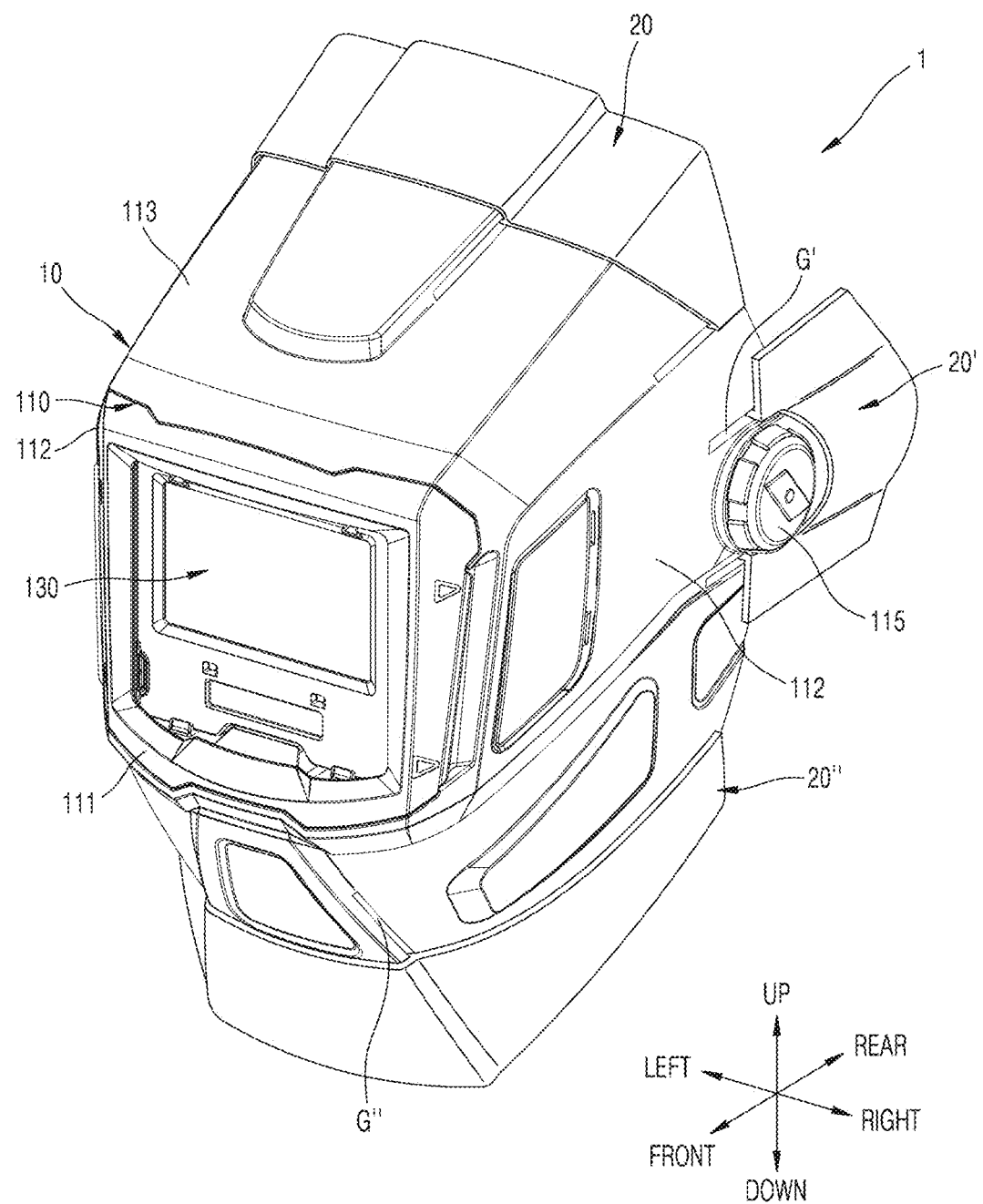
FIG. 4 is a perspective view schematically illustrating a protector for welding according to an embodiment of the present disclosure.

FIG. 4 is a perspective view schematically illustrating a protector for welding according to an embodiment of the present disclosure. FIG. 4 illustrates a plurality of auxiliary shields 20, 20', and 20", and one (hereinafter, referred to as a first auxiliary shield 20) of the auxiliary shields is the same as described above with reference to FIGS. 1 to 3C.

Referring to FIG. 4, other auxiliary shields (hereinafter, referred to as a second auxiliary shield 20' and a third auxiliary shield 20") may be arranged adjacent to both side surface portions 112 of the main body 110 of the face shield 10, respectively, or/and may be arranged adjacent to a lower portion of the front surface portion 111 of the main body 110.

The second and third auxiliary shields 20' and 20" are similar to the first auxiliary shield 20 described above with reference to FIGS. 1 to 30. For example, the second and third auxiliary shields 20' and 20" include protrusions, and the protrusions may be inserted into or coupled to grooves G' and G" formed in the main body 110. The grooves G' are formed in both side portions 112 of the main body 110, and another groove G" may be formed under the front surface portion 111. Each of the grooves G' and G" may extend in one direction, and the protrusions of the second and third auxiliary shields 20' and 20" may move linearly in one direction in a state of being inserted into or coupled to the corresponding grooves G' and G".

FIG. 4 illustrates that a plurality of second and third auxiliary shields 20' and 20" are arranged to correspond to the ears and neck of a welder, respectively, but the present disclosure is not limited thereto. In another embodiment, the protector for welding may include a pair of second auxiliary shields 20' corresponding to the ears of the welder. Alternatively, the protector for welding may include one third auxiliary shield 20" to correspond to the neck of the welder. Alternatively, the protector for welding may have various embodiments such as including one or two or more auxiliary shields selected from among the first to third auxiliary shields 20, 20' and 20".

FIG. 1 illustrates that the face shield 10 and the auxiliary shield 20 are coupled to each other by a coupling structure including a protrusion and a groove, but the present disclosure is not limited thereto. As in the embodiments to be described below, the auxiliary shield may be coupled to the face shield by various coupling structures.

Figure 5:
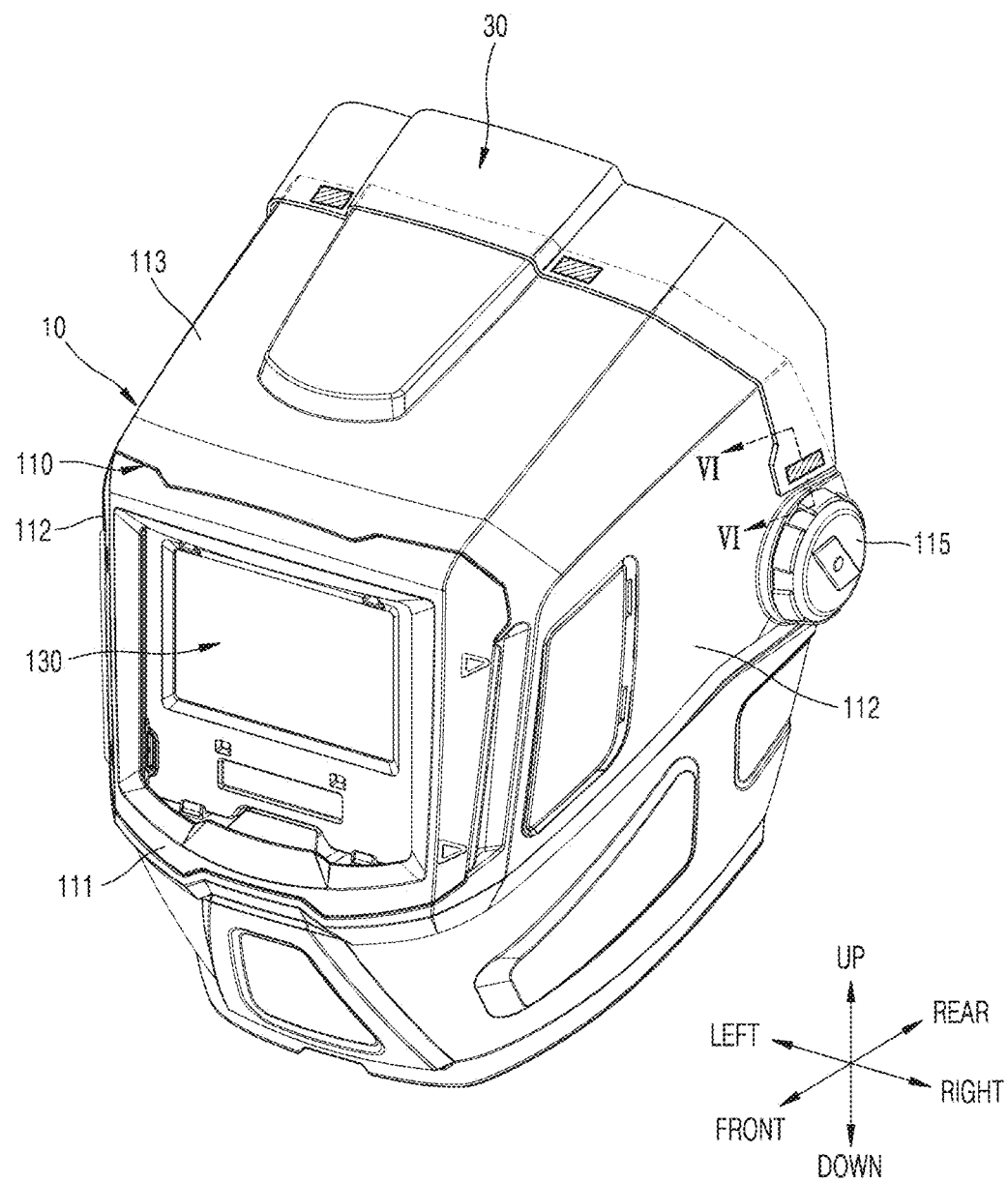
FIG. 5 is a perspective view schematically illustrating a protector for welding according to another embodiment of the present disclosure.
Figure 6:
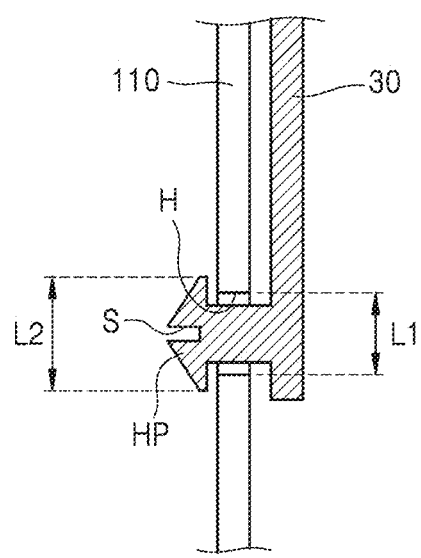
FIG. 6 is a cross-sectional view taken along line VI-VI' of FIG. 5.

FIG. 5 is a perspective view schematically illustrating a protector for welding according to another embodiment of the present disclosure, and FIG. 6 is a cross-sectional view taken along line VI-VI' of FIG. 5.

Referring to FIG. 5, the protector for welding includes a face shield 10 and an auxiliary shield 30, and the face shield 10 includes a main body 110 and a darkening 130 including a blackening filter. Although not illustrated in FIG. 5, the face shield 10 may include the wearing portion 120 (FIG. 5) described above with reference to FIG. 2. Since specific characteristics of the main body 110, the wearing portion, and the darkening section 130 are the same as described above, differences therebetween will be described below.

The auxiliary shield 30 is a configuration element which is injection-molded in a process separate from the face shield 10 and may include one or more of metal or plastic. The auxiliary shield 30 may be formed of a hard material capable of maintaining a shape thereof. The auxiliary shield 30 may include an element such as a spark that may occur during welding, and/or a material that is resistant to external impact. For example, the auxiliary shield 30 may include heat-resistant plastic or reinforced plastic.

The auxiliary shield 30 may be coupled to the face shield 10. One of the auxiliary shield 30 and the face shield 10 may include a hook-type protrusion, and the other may include a hole. In one embodiment, as illustrated in FIG. 6, the face shield 10 may include a hole H, and the auxiliary shield 30 may include a hook-type protrusion HP. The hook-type protrusion HP may be integral with the auxiliary shield 30.

The protrusion HP protrudes from the auxiliary shield 30 toward the face shield 10, and a width L2 of an end of the protrusion HP may be greater than a diameter L1 of the hole H. An incision line or a slit S may be provided at the end of the protrusion HP, thereby penetrating the hole H having a relatively small diameter. The protrusion HP penetrating the hole H has the width L2 of the end greater than the diameter L1 of the hole H, and thus, the auxiliary shield 30 may not be easily separated from the face shield 10 unless there is a separate external force.

A plurality of the protrusions HP and a plurality of the holes H of the auxiliary shield 30 and the face shield 10 may be provided along the edge of the main body 110 of the face shield 10. Although FIG. 5 illustrates that the auxiliary shield 30 is coupled to the face shield 10 to cover an upper side of the head of a welder, the present disclosure is not limited thereto. Similar to the above description made with reference to FIG. 4, a plurality of auxiliary shields 30 may be provided, and may be coupled to the face shield 10 so as to cover the upper side, ears, or/and neck of the head of the welder according to needs of the welder.

Figure 7:
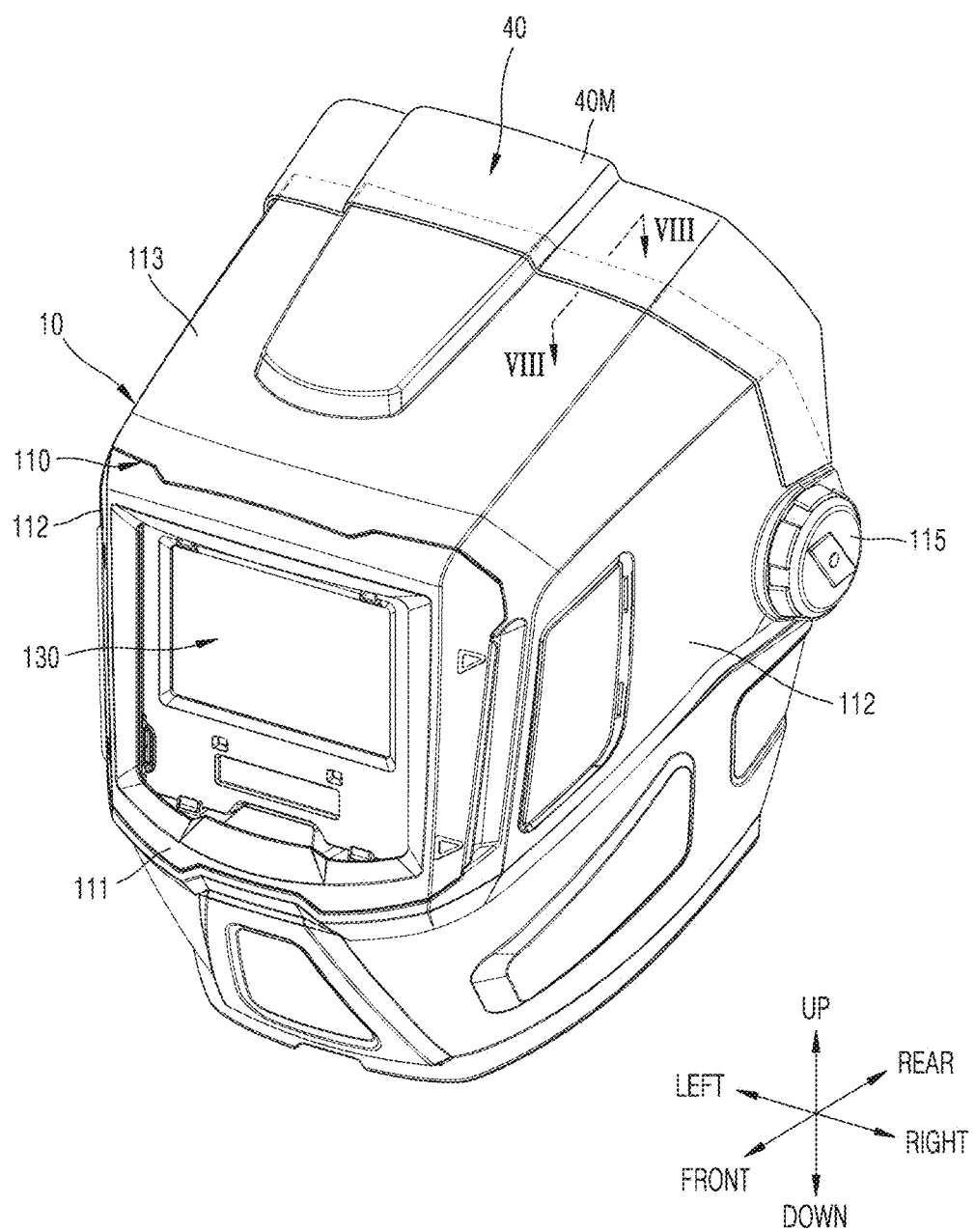
FIG. 7 is a perspective view schematically illustrating a protector for welding according to another embodiment of the present disclosure.
Figure 8A:
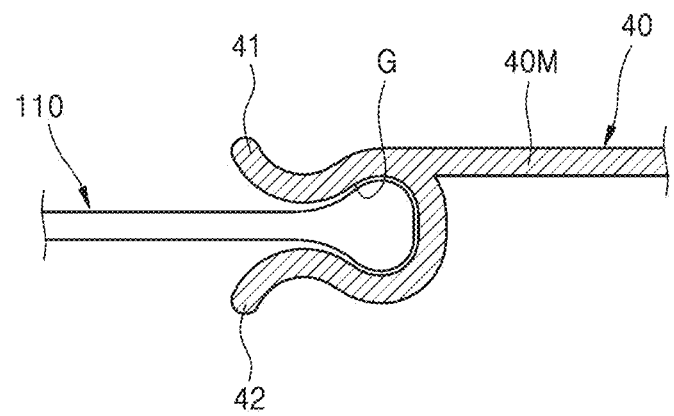
FIG. 8A is a cross-sectional view taken along line VIII-VIII' of FIG. 7.
Figure 8B:
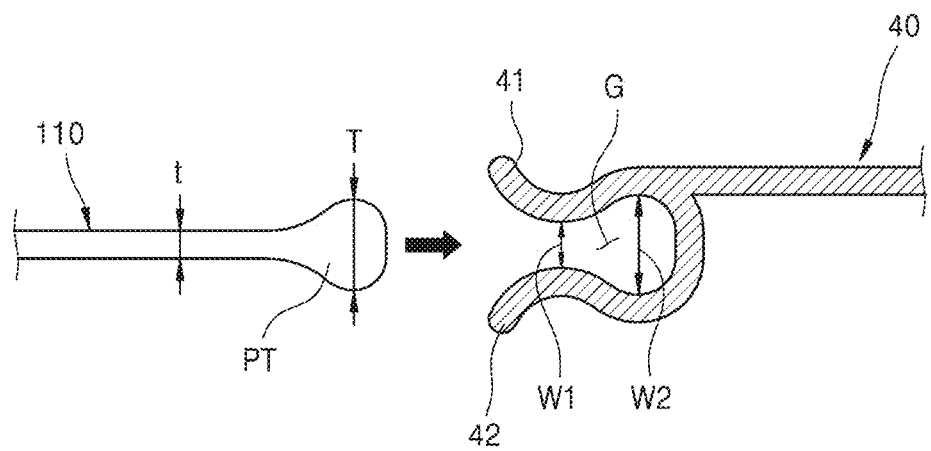
FIG. 8B is a cross-sectional view illustrating a state before a protrusion and a recess of FIG. 8A are coupled to each other.

FIG. 7 is a perspective view schematically illustrating a protector for welding according to another embodiment of the present disclosure, FIG. 8A is a cross-sectional view taken along line VIII-VIII' of FIG. 7, and FIG. 8B is a cross-sectional view illustrating a state before a protrusion and a recess of FIG. 8A are coupled to each other.

Referring to FIG. 7, the protector for welding includes a face shield 10 and an auxiliary shield 40, and the face shield 10 includes a main body 110 and a darkening section 130. Although not illustrated in FIG. 7, the face shield 10 may include the wearing unit 120 (FIG. 5) described above with reference to FIG. 2. Since specific characteristics of the main body 110, the wearing portion, and the darkening section 130 are the same as described above, differences therebetween will be described below.

The auxiliary shield 40 is a configuration element which is injection-molded in a process separate from the face shield 10 and may include one or more of metal or plastic. The auxiliary shield 40 may be formed of a hard material capable of maintaining a shape thereof. The auxiliary shield 40 may include an element such as a spark that may occur during welding, and/or a material that is resistant to external impact. For example, the auxiliary shield 40 may include heat-resistant plastic or reinforced plastic.

The auxiliary shield 40 may be coupled to the face shield 10. One of the auxiliary shield 40 and the face shield 10 may include a protrusion, and the other may include a recess for accommodating the protrusion.

In one embodiment, as illustrated in FIGS. 8A and 8B, the auxiliary shield 40 may be a clip type and may include part of a main surface portion 40M for example, one end 41 of the main surface portion, and one end 41 of the main surface portion 40M and a branch portion 42 extending from the one end 41 of the main surface portion 40M which are connected to each other while defining a groove G therein. The one end 41 of the main surface portion and the branch portion 42 may form an approximately C shape having one side open and the groove G formed therein, in some embodiments, the groove G defined as a gap between the one end 41 of the main surface portion 40M and the branch portion 42 may have a shape in which an outer first width W1 is smaller than an inner second width W2.

The main body 110 may include a protrusion PT inserted into the groove G of the auxiliary shield 40. The protrusion PT may be a structure integrally injected with the main body 110 and may be understood as an edge of one side of the main body 110. The protrusion PT may have a second thickness T greater than a first thickness t of the main body 110.

Before the protrusion PT is inserted into the groove G or when no external force is applied to the groove G, the outer first width W1 is smaller than the second thickness T of the protrusion PT. When the protrusion PT may be inserted into the groove G, the one end 41 of the main surface portion 40M and the branch 42 may be further separated from each other to increase a gap therebetween and then the first width W1 temporarily may be increased. When the protrusion PT is inserted into the groove G, the protrusion PT may provide a force to push the one end 41 of the main surface portion 40M and the branch portion 42 to each other, and a curved or rounded one end 41 of the main surface portion 40M and the branch portion 42 may move in a direction in which the gap therebetween is increased by an external force applied by the protrusion PT. After the protrusion PT passes through the outside of the groove G, the protrusion PT having the second thickness T is accommodated inside the groove G, for example, inside the groove G having the second width W2. The second width W2 may be equal to or greater than the second thickness T of the protrusion PT.

Since the one end 41 of the main surface portion 40M and the branch portion 42 have rounded or curved shapes such that a gap therebetween is widened towards the outside, when the protrusion PT is inserted thereinto, the protrusion PT may be smoothly inserted into the groove G along a contact surface of the one end 41 of the main surface portion 40M and the branch portion 42 while the protrusion PT is in contact with the one end 41 of the main surface portion 40M and the branch portion 42.

After the protrusion PT is accommodated in the groove G, the one end 41 of the main surface portion 40M and the branch 42 having temporarily increased gap therebetween are returned to original states. For example, the first width W1 between the one end 41 of the main surface portion 40M and the branch portion 42 is temporarily increased when the protrusion PT is inserted, and then is returned to an original state. The protrusion PT may be separated from the groove G, and in this case, even when the protrusion PT is pulled in a direction away from the groove G, the first width W1 between the one end 41 of the main surface portion 40M and a branch portion 42 may be temporarily increased and then returned to an original state.

The embodiments described with reference to FIGS. 7 to 8B describe that the main body 110 of the face shield 10 includes the protrusion PT and the auxiliary shield 40 includes the groove G, but in another embodiment, The face shield 10 may include a recess and the auxiliary shield 40 may include a protrusion.

Figure 8C:
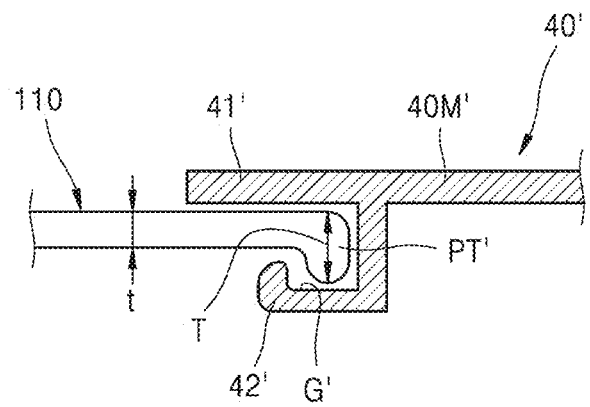
FIG. 8C corresponds to a modification embodiment of FIG. 8A.

FIG. 8C corresponds to a modification embodiment of FIG. 8A.

Referring to FIG. 8C, the main body 110 may include a protrusion PT' to be inserted into a groove G' of an auxiliary shield 40'. The protrusion PT' is a structure that is integrally injected with the main body 110 and may be understood as an edge of one side of the main body 110. The protrusion PT' may have a second thickness T' greater than a first thickness t' of the main body 110.

The face shield 10' may include a first piece 41' and a second piece 42' connected to each other while defining a groove G' therein. One end 41' of the main surface portion 40M' may be understood as an edge of one side of the main surface portion 40M' of the auxiliary shield 40'. The groove G' defined by the one end 41' of the main surface portion 40M' and a branch portion 42' may have a shape in which an outer first width is smaller than an inner second width.

However, one end 41' of the main surface portion 40M' and the branch portion 42' may not have rounded or curved shapes as illustrated in FIGS. 8A and 8B. The branch portion 42' may have an approximately L-shape. For example, a first portion of the branch portion 42' may extend in a direction (for example, a vertical direction) crossing one end 41' of the main surface portion 40M', and a second portion may be bent from the first portion and extend substantially parallel to the one end 41' of the main surface portion 40M'.

When the protrusion PT is inserted, a gap between the one end 41' of the main surface portion 40M' and the branch portion 42' is temporarily increased and then returned to an original shape, a structure in which the protrusion PT' having the second thickness T' is accommodated in the groove G' is the same as described above with reference to FIGS. 8A and 8B.

A plurality of structures of the protrusions PT and PT' and the groove G of the auxiliary shields 40 and 40' and the face shield 10 may be provided along an edge of the main body 110 of the face shield 10. FIG. 7 illustrates that the auxiliary shield 40 is coupled to the face shield 10 to cover an upper side of the head of the welder, but the present disclosure is not limited thereto. Similar to the above description made with reference to FIG. 4, a plurality of auxiliary shields 40 and 40' may be provided and may be coupled to the face shield 10 to cover the upper side, ears, or/and neck of the head of the welder according to needs of the welder.

Figure 9:
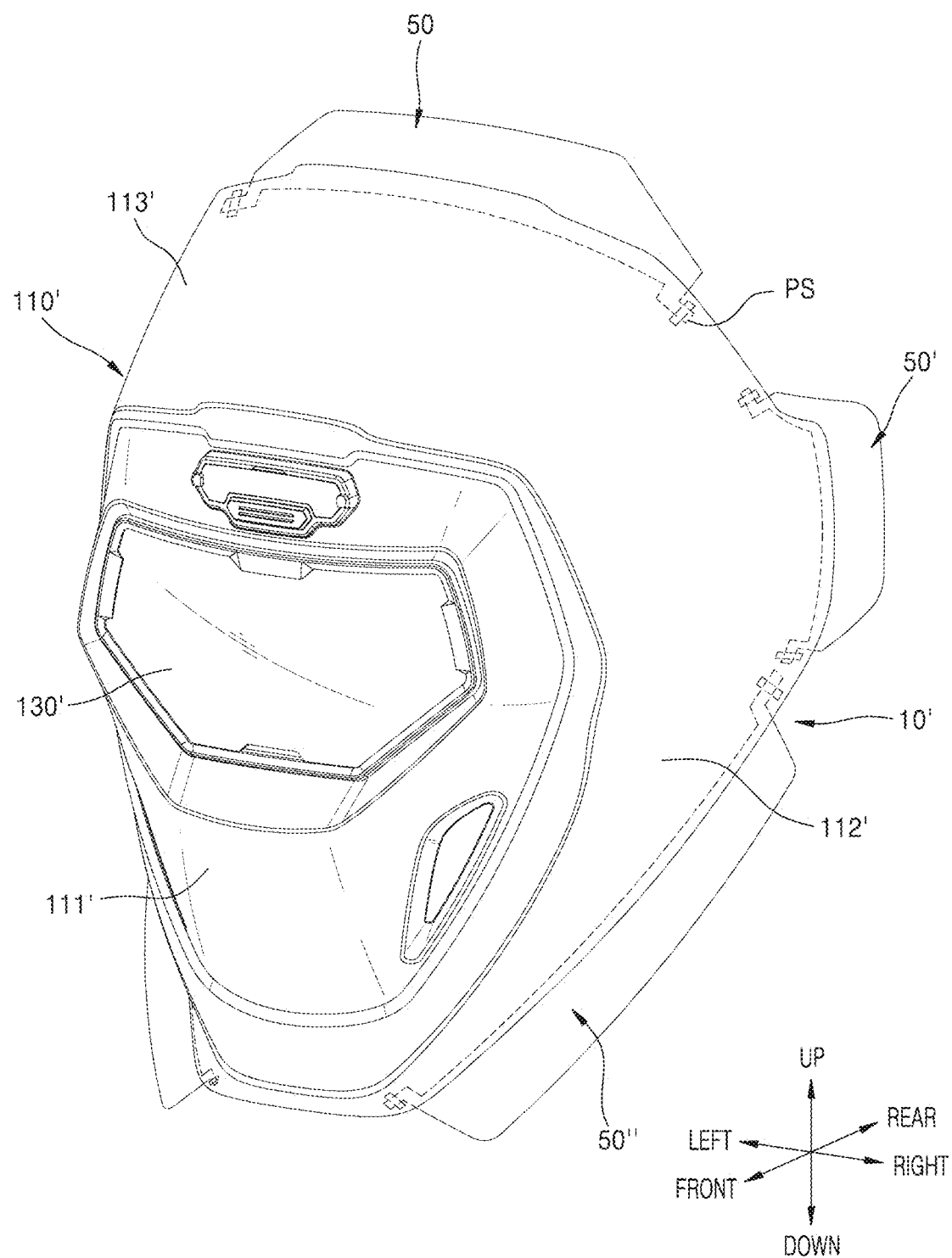
FIG. 9 is a perspective view schematically illustrating a protector for welding according to another embodiment of the present disclosure.
Figure 10:
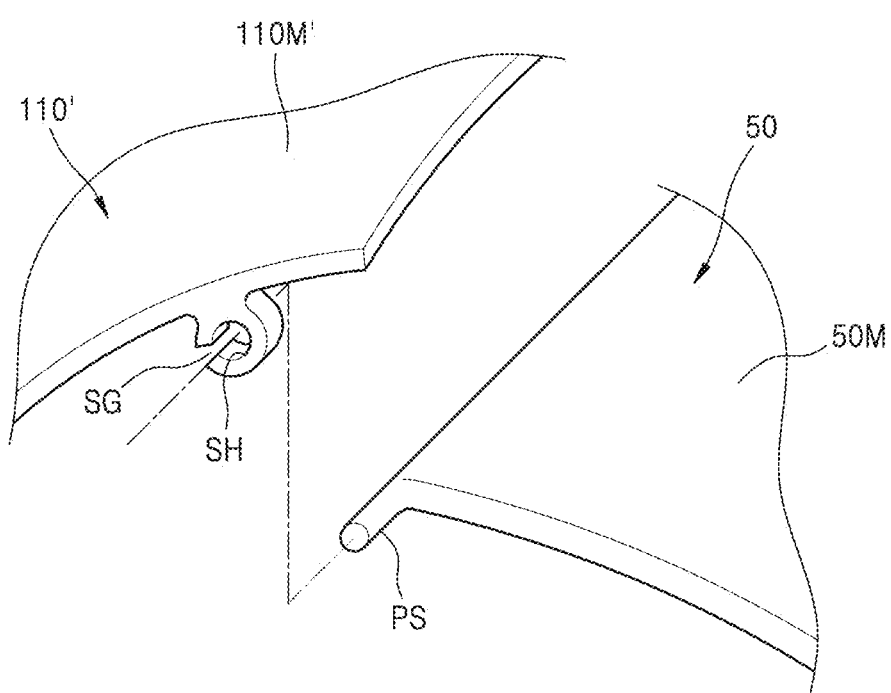
FIG. 10 is a side perspective view illustrating part of a main body of a face shield and part of an auxiliary shield.

FIG. 9 is a perspective view schematically illustrating a protector for welding according to another embodiment of the present disclosure, and FIG. 10 is a side perspective view illustrating part of a main body of a face shield and part of an auxiliary shield.

Referring to FIG. 9, the protector for welding includes a face shield 10' and an auxiliary shield 50. The face shield 10' includes a main body 110' and a darkening section 130', and the darkening section 130' is the same as described above with reference to FIG. 1. Although not illustrated, the main body 110' may be connected to a wearing portion, and the protector for welding may be worn on the head of the welder by the wearing portion. As described above with reference to FIGS. 1 and 2, the wearing portion may be a headgear strap or an elastic band-type strap.

The main body 110' may include a front surface portion 111' corresponding to the eyes, nose, and/or mouth of the welder, side surface portions 112' that are bent with respect to and the front surface portion 111' and arranged on the left and right sides of the front surface portion 111' and an upper surface portion 113' arranged above the front surface portion 111' The side surface portions 112 ' and the upper surface portion 113' may each extend in a direction away from the front surface portion 111' while being bent at the front surface portion 111', and thus, the main surface of the main body 110' may protect the three-dimensional face of the welder in three dimensions.

The protector for welding may include a plurality of auxiliary shields 50, 50', and 50", and the plurality of auxiliary shields 50, 50', and 50" may be coupled to the face shield 10'. For example, the first auxiliary shield 50 may cover the head (for example, frontal and/or parietal) of a user, and the second auxiliary shield 50' may cover a vicinity of the ear (for example, a temporal region), and the third auxiliary shield 50" may cover a vicinity of the chin.

The first to third auxiliary shields 50, 50', and 50" may include protrusions, and the face shield 10' may include holes for accommodating the protrusions. Alternatively, the first to third auxiliary shields 50, 50', and 50" may include holes, and the face shield 10' may include protrusions.

For example, as illustrated in FIG. 10, the main body 110' of the face shield 10' may include holes SH arranged inside with respect to the main surface portion 110M' covering the head of the welder, and the first auxiliary shield 50 may include protrusions PS.

The protrusions PS may be arranged on both side edges of a main surface portion 50M of the first auxiliary shield 50, and the protrusions PS may be inserted into the holes SH. The holes SH may each include an incision portion SG formed on one side as illustrated in FIG. 10, and with this structure, the protrusions PS may be easily inserted into the holes SH.

The first auxiliary shield 50 may be a configuration element injection-molded in a separate process from the face shield 10' and may include one or more of metal or plastic. The auxiliary shield 50 may be formed of a hard material capable of maintaining an original shape. The auxiliary shield 50 may include an element such as welding spatter or spark, which may occur during welding, and/or a material that is resistant to external impact. For example, the auxiliary shield 50 may include heat-resistant plastic or reinforced plastic.

The first auxiliary shield 50 may move such that an overlapping area with the main body 110' is increased or is decreased according to selection of the welder. An increase and a decrease in overlapping area between the first auxiliary shield 50 and the main body 110' will be described with reference to FIGS. 11A to 13B below.

Figure 11A:
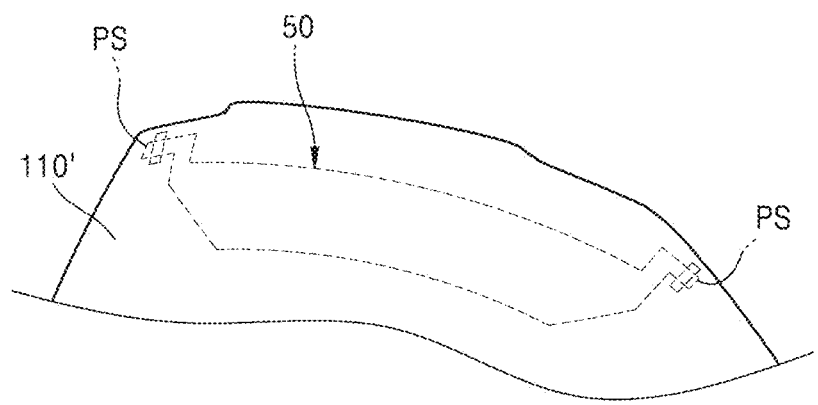
FIG. 11A illustrates part of a protector for welding according to an embodiment of the present disclosure.
Figure 11B:
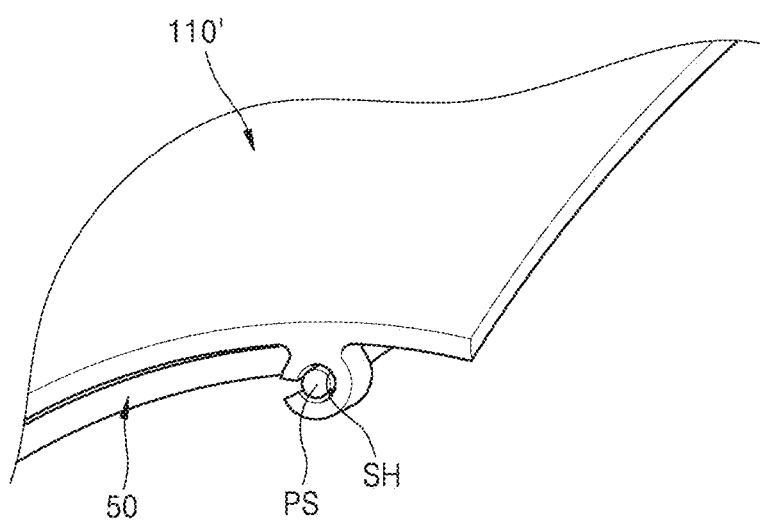
FIG. 11B is a side perspective view illustrating a partial configuration of FIG. 11A.

FIG. 11A is part of the protector for welding illustrating a first state in which the overlapping area of the auxiliary shield 50 and the main body 110' is relatively large, and FIG. 11B is a side perspective view of part of the auxiliary shield 50 and part of the main body 110' which are extracted in the first state.

As illustrated in FIG. 11A, in the first state, the first auxiliary shield 50 may be located on an inner surface of the main body 110' and may be arranged to overlap the main body 110'. In this case, protrusions PS of the first auxiliary shield 50 may overlap the main body 110' while being inserted into the hole SH as illustrated in FIG. 11B.

Figure 12A:
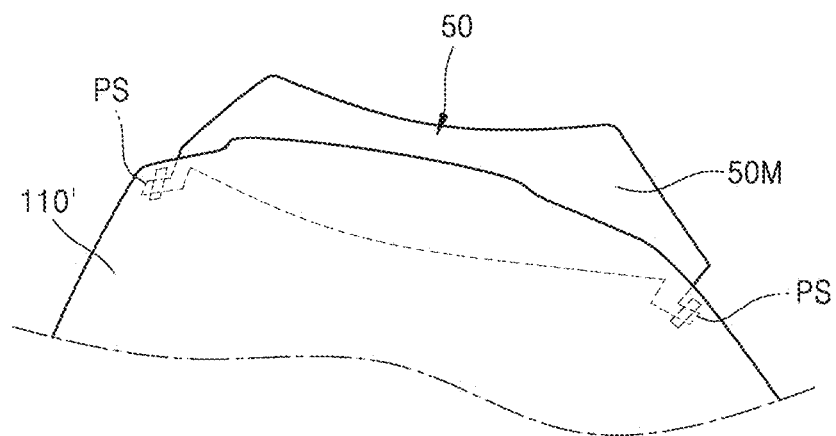
FIG. 12A illustrates part of a protector for welding according to another embodiment of the present disclosure.
Figure 12B:
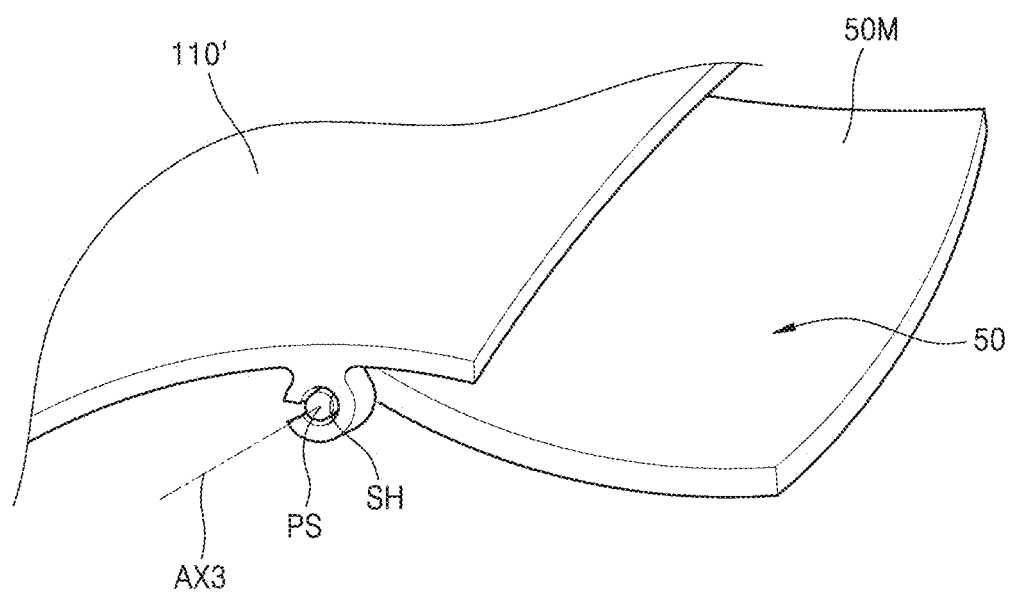
FIG. 12B is a side perspective view illustrating a partial configuration of FIG. 12A.

FIG. 12A illustrates part of the protector for welding representing a second state in which the overlapping area of the first auxiliary shield 50 and the main body 110' is relatively small, and FIG. 12B is a side perspective view of part of the auxiliary shield 50 and part of the main body 110' in the second state.

As illustrated in FIG. 12A, in the second state, the first auxiliary shield 50 may extend in a direction away from one edge of the main body 110' and may cover part of the head of the welder which is not covered by the main body 110'. For example, since the protrusion PS overlapping with the main body 110' rotates in place around an axis AX3 penetrating the center of the hole SH while being inserted into or coupled to the hole SH as illustrated in FIG. 11B, the first auxiliary shield 50 may be located to extend in a direction away from one side of the main body 110' as illustrated in FIG. 11B. That is, the first auxiliary shield 50 may also rotate according to the rotation of the protrusion PS. As the protrusion PS rotates, the first auxiliary shield 50 may have a reduced area overlapping with the main body 110' as illustrated in FIG. 12B, and the main surface portion 50M of the first auxiliary shield 50 may extend in a direction away from one edge of the main body 110.

In some embodiments, the main surface portion 50M of the first auxiliary shield 50 may include a curved surface in the second state as illustrated in FIGS. 12A and 12B. In one embodiment, the main surface portion 50M may include a curved surface that is convex toward the head of the welder as illustrated in FIGS. 12A and 12B. The main surface portion 50M of the first auxiliary shield 50 may receive an external force in the second state, and a curve direction may be changed as in a third state to be described below.

Figure 13A:
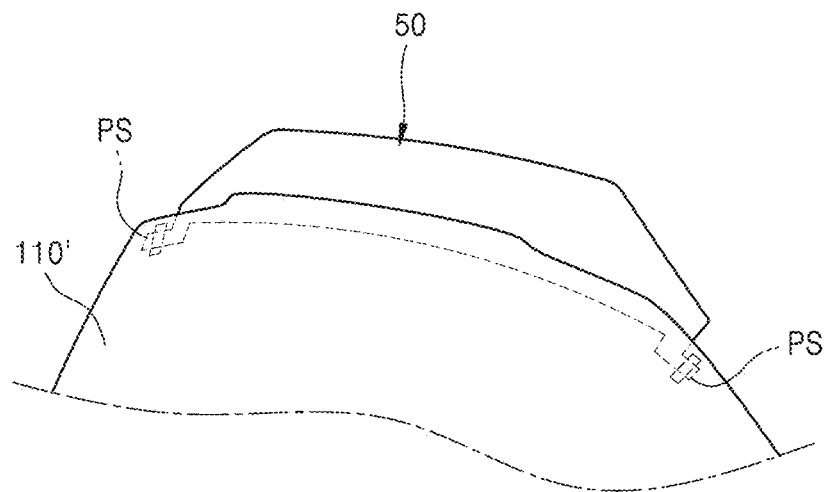
FIG. 13A illustrates part of a protector for welding according to another embodiment of the present disclosure.
Figure 13B:
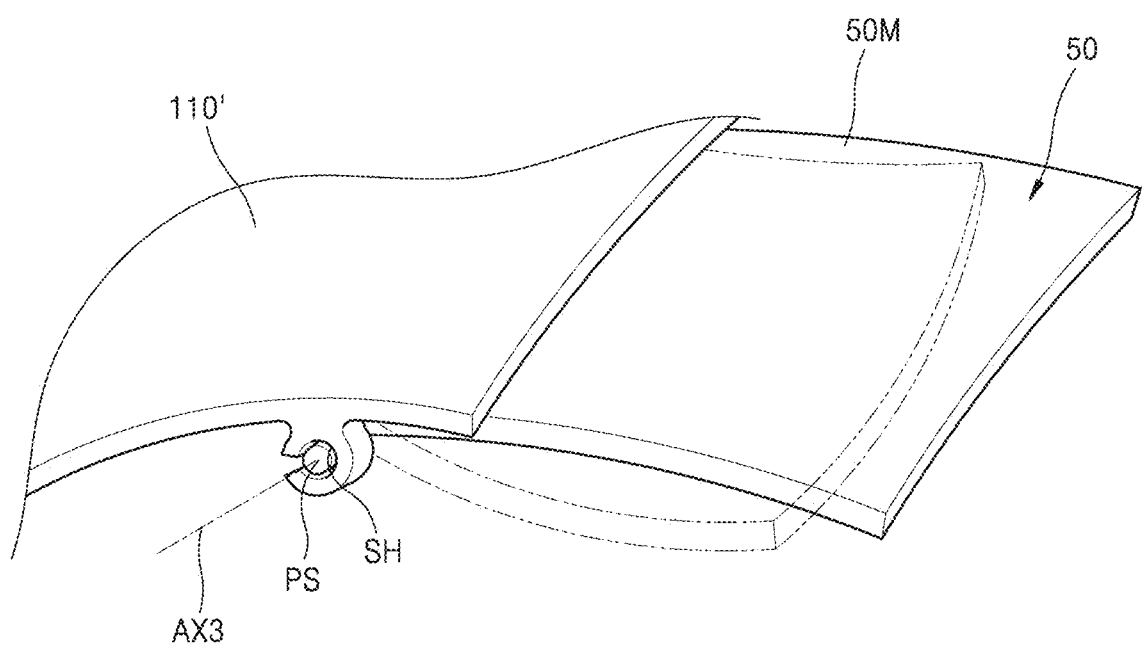
FIG. 13B is a side perspective view illustrating a partial configuration of FIG. 13A.

FIG. 13A illustrates part of the protector for welding representing the third state in which an overlapping area of the first auxiliary shield 50 and the main body 110' is relatively small, and FIG. 13B is a side perspective view of part of the first auxiliary shield 50 and part of the main body 110' in the third state.

The curve direction of the curved main surface portion 50M illustrated in FIGS. 12A and 12B may be caused by maintaining the shape of the main surface portion of the auxiliary shield 50 arranged inside the main body 110' in the first state.

Thereafter, when a predetermined external force (for example, a force of the welder) is applied, the main surface portion 50M of the first auxiliary shield 50 in the second state has an opposite curve direction as illustrated in FIGS. 13A and 13B. For example, the main surface portion 50M of the first auxiliary shield 50, which is convexly curved toward the head of the welder as illustrated in FIG. 12B, may be changed in a direction away from the head of the welder, for example, to a surface that is convexly curved toward the outside, as illustrated in FIG. 13B.

Characteristics of the first auxiliary shield 50 described with reference to FIGS. 10 to 13B may be equally applied to the second and third auxiliary shields 50' and 50" illustrated in FIG. 9.

FIGS. 14A to 14D are side views of a user wearing the protector for welding according to embodiments of the present disclosure.

Referring to FIGS. 14A to 14D, the main body 110 of the face shield 10 may protect the face of a user USH. The main body 110 of the face shield 10 may be coupled to a wearing portion 120, and the main body 110 covers the face of the user USH by wearing the wearing portion 120 on the head. A structure of the main body 110 may be substantially the same as the structure of the main bodies 110 and 110' previously described with reference to FIG. 1 or FIG. 9, and a structure of the wearing portion 120 may be substantially the same as the structure of the wearing portion 120 described above with reference to FIGS. 1 and 2.

Figure 14A:
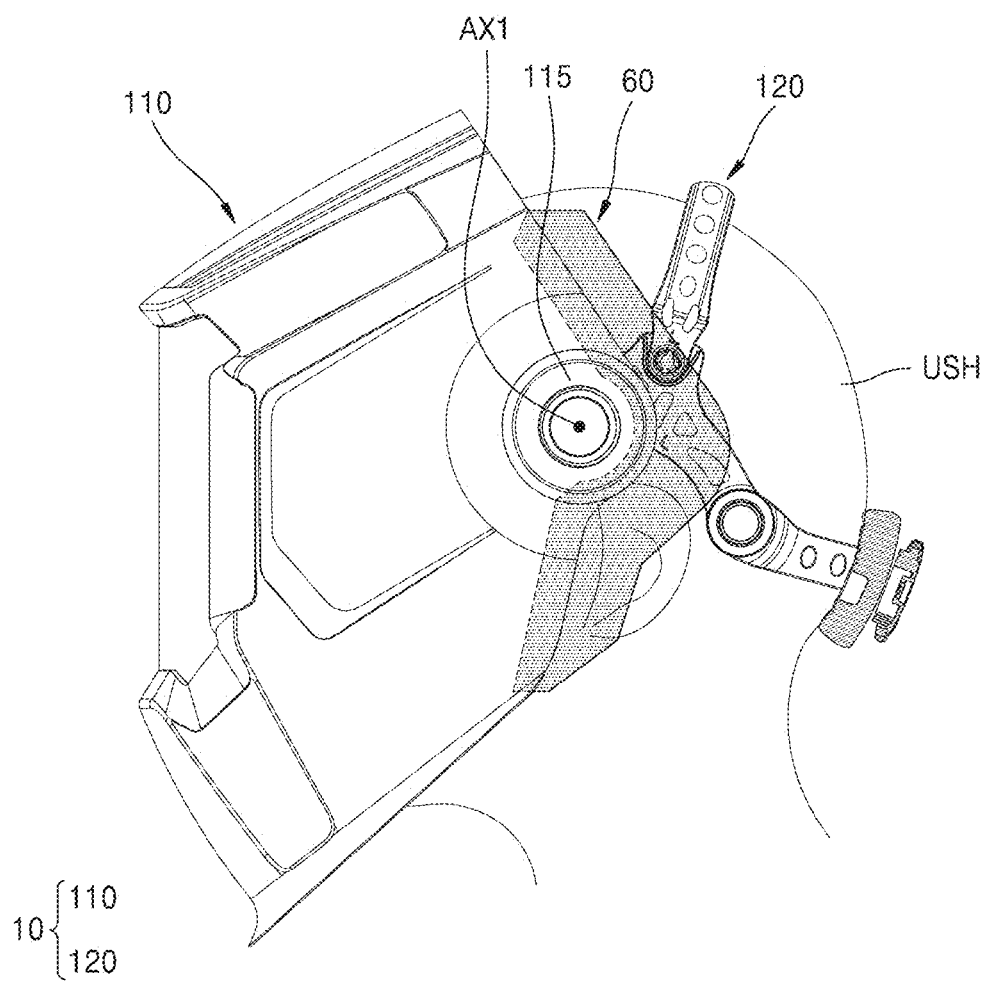
FIGS. 14A to 14D are side views of a user wearing a protector for welding, according to embodiments of the present disclosure.
Figure 14B:
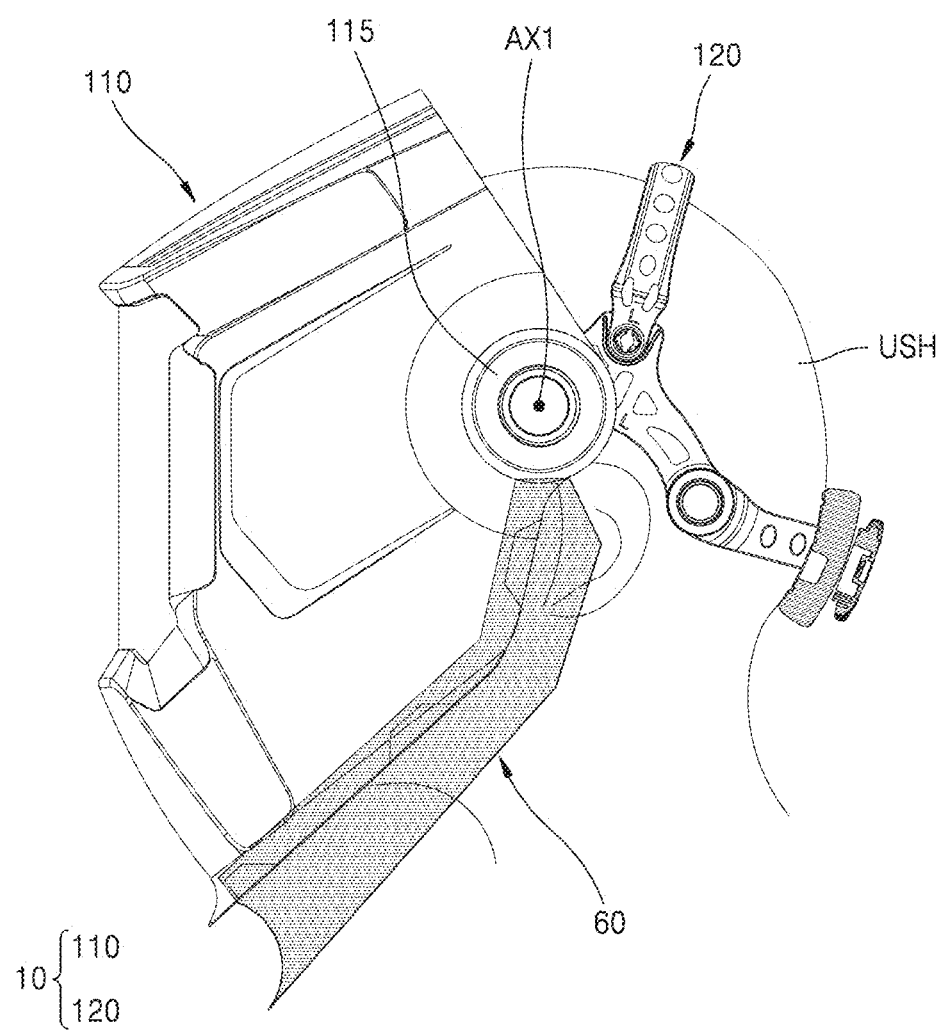

As illustrated in FIG. 14A, an auxiliary shield 60 may cover the ear of the user USH and a vicinity of the ears. When viewed from the side, the auxiliary shield 60 may have a shape that partially surrounds a first pivot portion 115 through which a rotation axis AX1 of the main body 110 passes. The auxiliary shield 60 may cover a vicinity of the chin of the user USH on the side view as illustrated in FIG. 14B and may be arranged on the rotation axis AX1 of the main body 110 or a lower side of the first pivot portion 115.

Figure 14C:
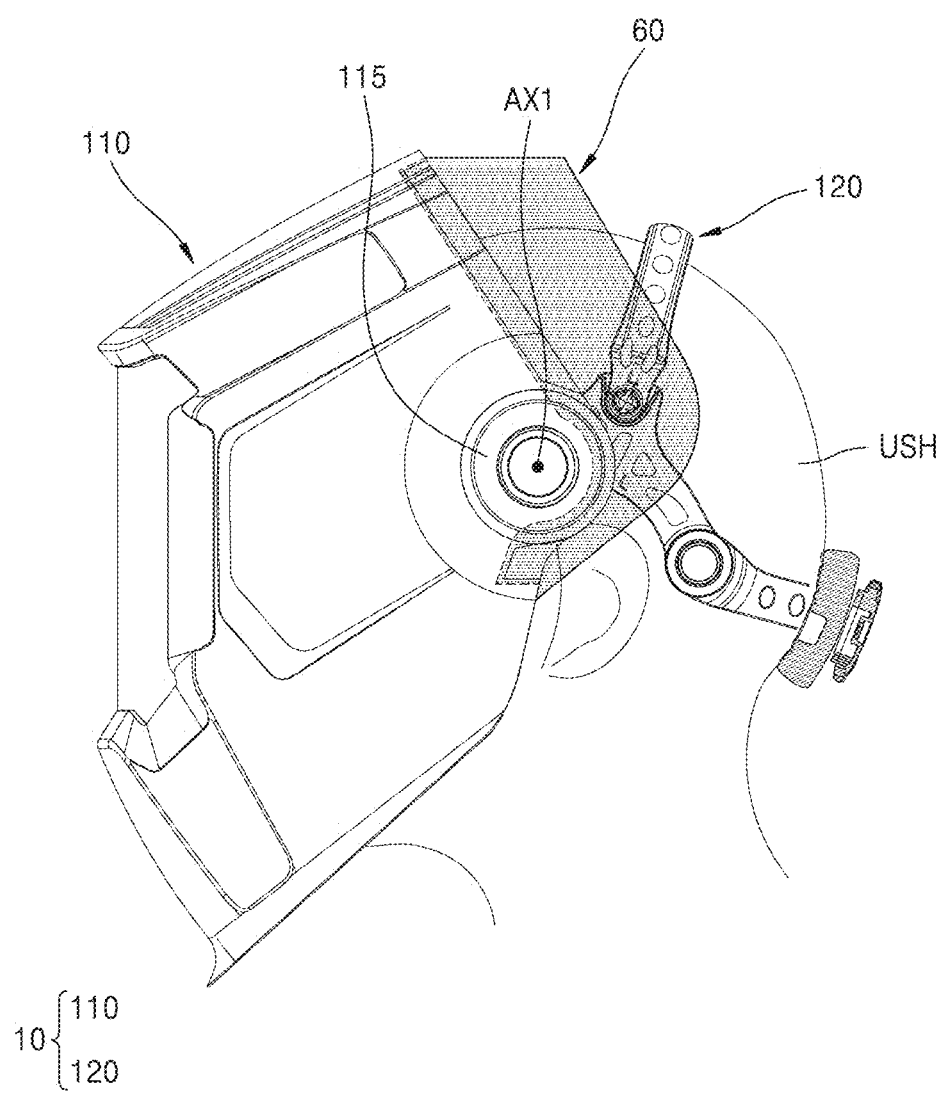

The auxiliary shield 60 may cover part of the head of the user USH as illustrated in FIG. 14C. Both ends of the auxiliary shield 60 may have a shape partially surrounding the first pivot portion 115 through which the rotation axis AX1 of the main body 110 passes.

Figure 14D:
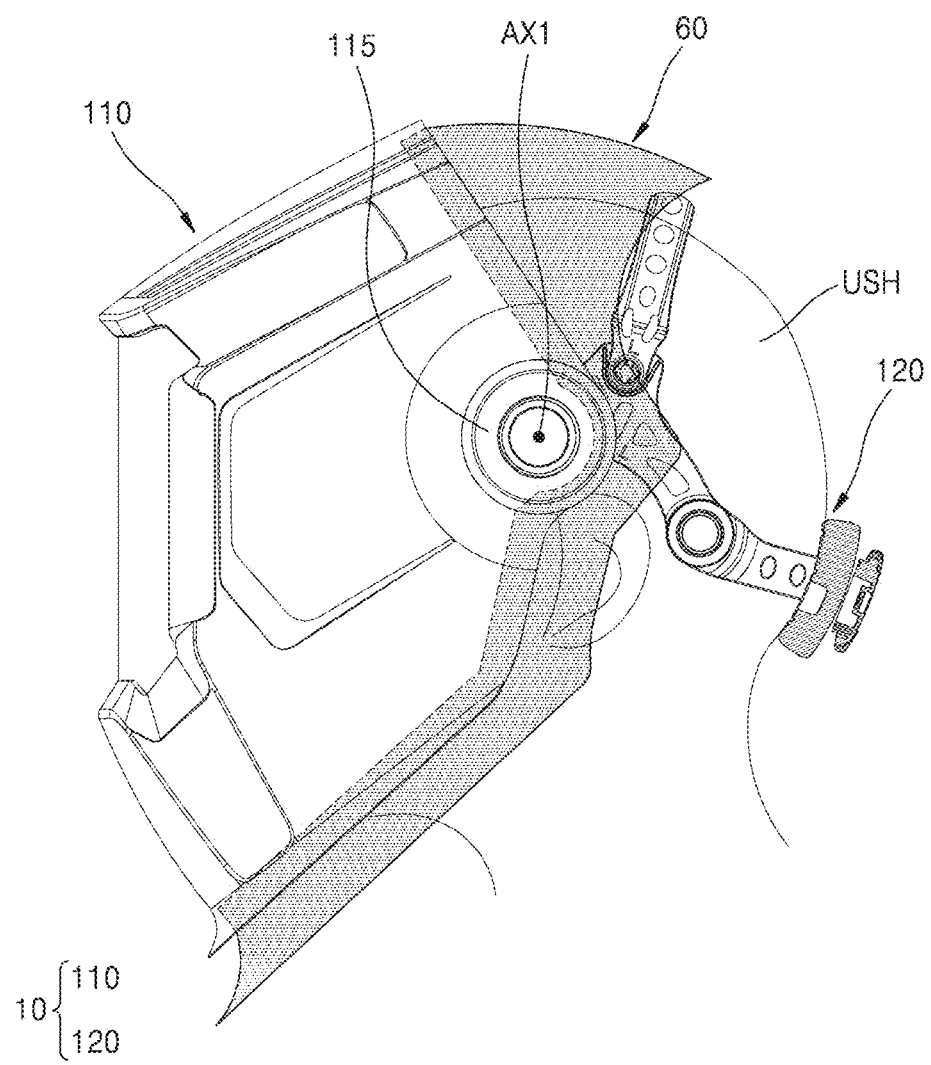

As illustrated in FIG. 14D, the auxiliary shield 60 may cover an upper portion (for example, part of the occipital portion) of the head of the user USH, part of the temporal portion, and a vicinity of the chin. The auxiliary shield 60 may be formed as one body and may be coupled to the main body 110.

FIGS. 15A to 15D are cross-sectional views illustrating coupling between a main body of a face shield and an auxiliary shield included in a protector for welding according to embodiments of the present disclosure.

Figure 15A:
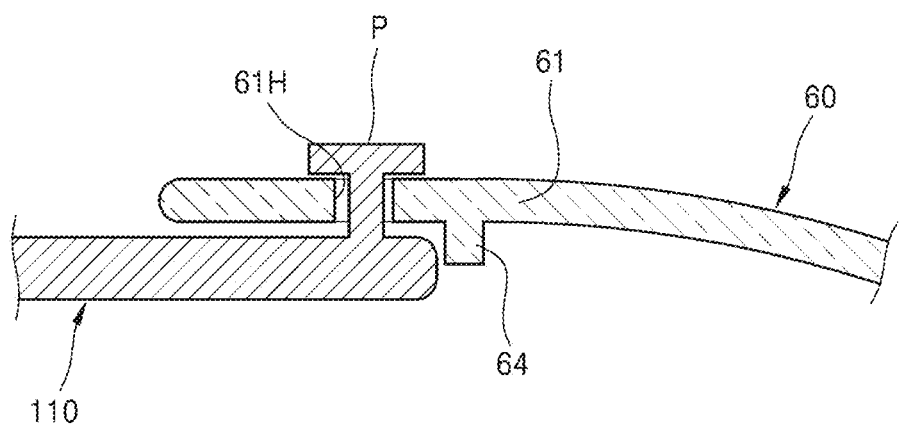
FIGS. 15A to 15D are cross-sectional views illustrating coupling between a main body of a face shield and an auxiliary shield included in a protector for welding, according to embodiments of the present disclosure.

Referring to FIG. 15A, the main body 110 may include a protrusion P arranged adjacent to an edge of the main body 110, and the protrusion P may be coupled to a hole 61H of the auxiliary shield 60. The protrusion P may have an approximately "T" shape in cross section.

The auxiliary shield 60 may include a first branch portion 64 protruding from one end 61 of a main surface portion partially overlapping the main body 110 in a direction (for example, a thickness direction) crossing an extension direction of the one end 61 of the main surface portion. The first branch portion 64 is a type of protrusion, and the first branch portion 64 of the auxiliary shield 60 may be arranged adjacent to the edge of the main body 110.

The first branch portion 64 of the auxiliary shield 60 may have a function of a stopper when the main body 110 and the auxiliary shield 60 are coupled to each other, and/or the auxiliary shield 60 or the main body 110 may be prevented from rotating with respect to each other in a state in which the auxiliary shield 60 and the main body 110 are coupled to each other. For example, in a state in which the protrusion P and the hole 61H are coupled to each other, the auxiliary shield 60 rotates at a predetermined angle with respect to the main body 110 around a virtual vertical axis penetrating the protrusion P and the hole 61H or may be prevented from rotating with respect to the main body 110.

Figure 15B:
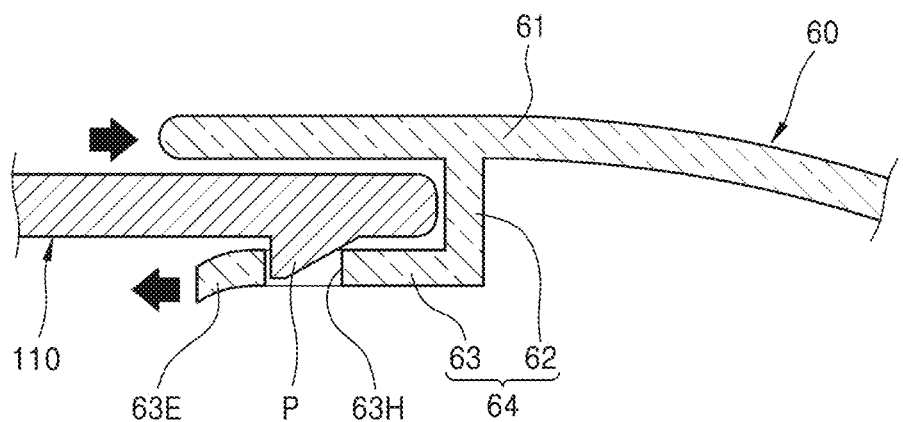

Referring to FIG. 15B, the auxiliary shield 60 may include one end 61 of a main surface portion and a first branch portion 64 protruding from the one end 61 of the main surface portion. The first branch portion 64 may include a first portion 62 extending in a direction crossing the one end 61 of the main surface portion, and a second portion 63 which is connected to the first portion and extends in the same direction as the one end 61 of the main surface portion, and the first portion 62 and the second portion 63 may form an approximately "L" shape. The first branch portion 64 may be integrally formed with the one end 61 of the main surface portion, and the one end 61 of the main surface portion and the first branch portion 64 form an approximately "C" shape having one side open.

The main body 110 may include a protrusion P arranged adjacent to the edge of the main body 110, and the protrusion P may be coupled to a hole 63H of the auxiliary shield 60. The hole 63H may be formed in part of the first branch portion 64, for example, in the second portion 63.

An edge of the first branch portion 64, for example, an edge region 63E of the second portion 63 may include an inclined surface. The main body 110 and the auxiliary shield 60 may move toward each other such that part of the main body 110 is inserted between the one end 61 of the main surface portion of the auxiliary shield 60 and the first branch portion 64. The protrusion P of the main body 110 may have a wedge shape (or a triangle) whose thickness decreases toward the edge of the main body 110, and since an edge region 63E of the second portion 63 of the first branch portion 64 includes an inclined surface, the wedge-shaped protrusion P may smoothly move toward the first portion 62 while in contact with the second portion 63. Thereafter, the protrusion P may be coupled to the hole 63H of the second portion 63.

FIG. 15B illustrates that a second portion 63 of the first branch portion 64 has a predetermined length such that an edge region 63E of the second portion 63 of the first branch portion 64 is arranged adjacent to an edge region of the one end 61 of the main surface portion. In another embodiment, referring to FIG. 15C, a length of the second portion 63 of the first branch portion 64 may be formed to be relatively short.

Figure 15C:
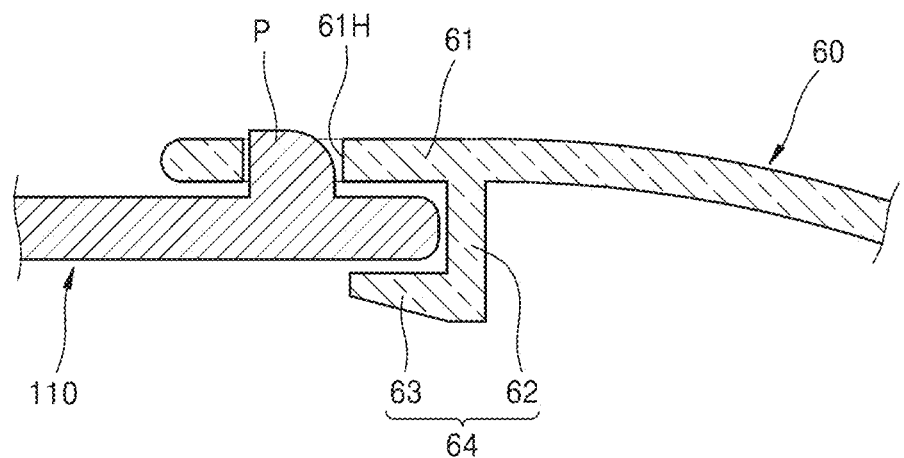

Referring to FIG. 15C, a protrusion P of the main body 110 may be coupled to a hole 61H formed in one end 61 of the main surface portion of the auxiliary shield 60. The protrusion P may include a round surface, and when coupling to the hole 61H, the protrusion P may be smoothly inserted along the round surface of the protrusion P.

Figure 15D:
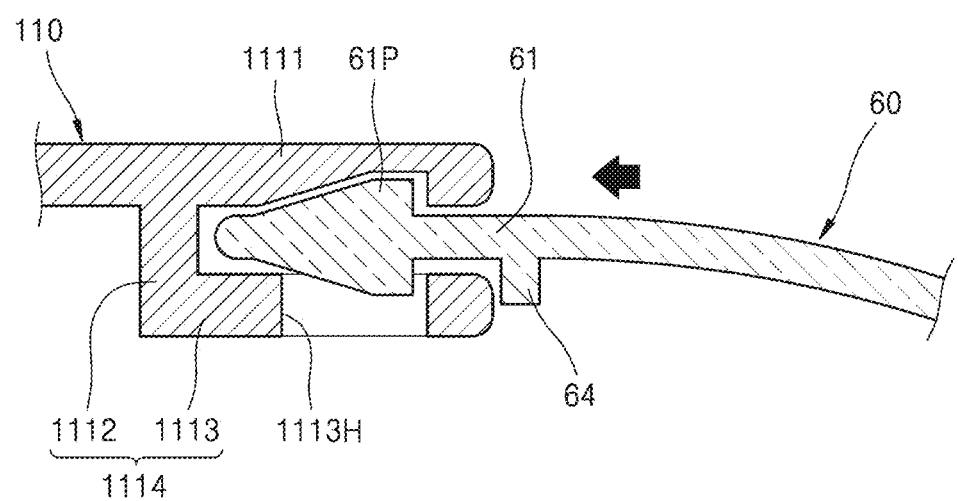

Referring to FIG. 15D, the main body 110 may include part (for example, one end 1111 of the main surface portion) of the main surface portion and a second branch portion 1114 protruding from the one end 1111 of the main surface portion. The second branch portion 1114 may include a first portion 1112 extending in a direction crossing the one end 1111 of the main surface portion and a second portion 1113 that is connected to the first portion 1111 and extends in substantially the same direction as the one end portion 1111 of the main surface portion, and the first portion 1112 and the second portion 1113 may form an approximately "L" shape. The second branch portion 1114 may be formed integrally with the one end 1111 of the main surface portion, and the main surface portion 1111 and the second branch portion 1114 may form an approximately "C" shape having one side open.

The auxiliary shield 60 includes a protrusion 61P, and the protrusion 61P may have a shape of a horn (for example, a cone) whose cross-sectional area gradually decreases toward the main body 110. The main surface portion 1111 of the main body 110 may include a groove formed therein to accommodate art of the protrusion 61P, and a second portion 1113 of the second branch portion 1114 may include a hole 1113H to accommodate the other portion of the protrusion 61P. When the main body 110 and the auxiliary shield 60 are coupled to each other, the auxiliary shield 60 may include a first branch portion 64 having a protrusion shape adjacent to one end 61 of the main surface portion to be arranged adjacent to the edge of the second branch portion 1114. The first branch portion 64 may have a short length and may be a type of protrusion.

Figure 15E:
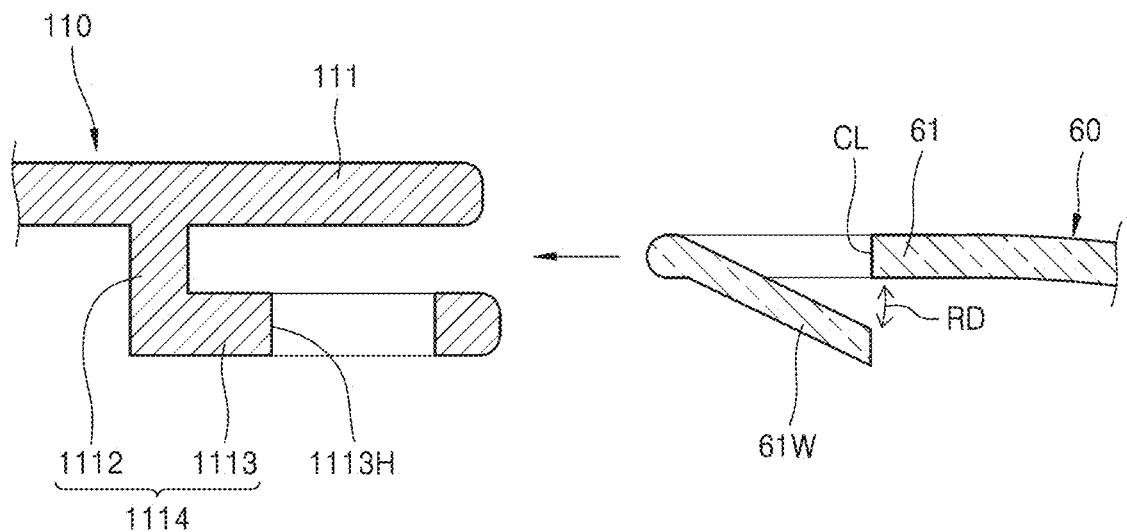
FIG. 15E is a view illustrating a state before the auxiliary shield and the main body are coupled to each other in the protector for welding according to an embodiment of the present disclosure.
Figure 15F:
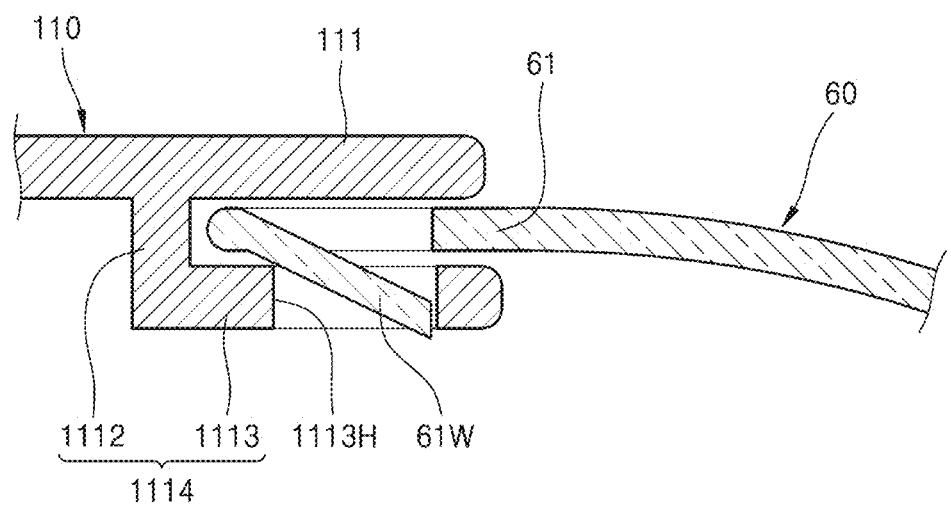
FIG. 15F is a cross-sectional view illustrating a state after the coupling.
Figure 15G:
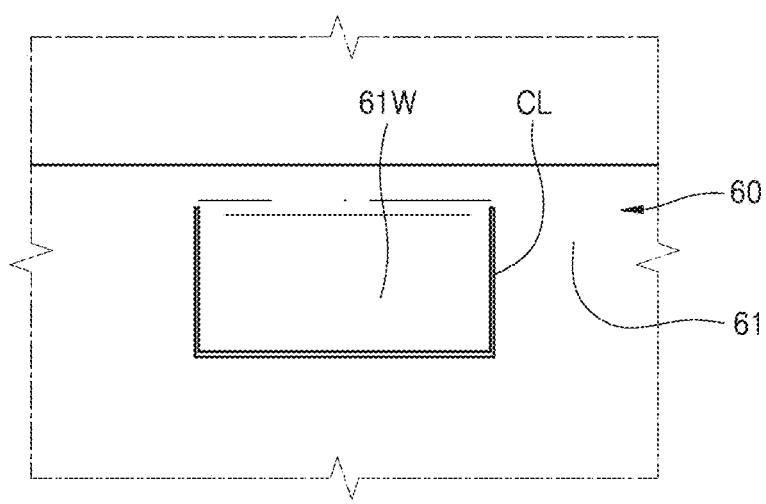
FIG. 15G is a plan view illustrating part of the auxiliary shield.

FIG. 15E illustrates a state before an auxiliary shield and a main body are coupled to each other in a protector for welding according to an embodiment of the present disclosure, FIG. 15F is a cross-sectional view after the coupling, and FIG. 15G is a plan view illustrating part of the auxiliary shield.

Referring to FIGS. 15E and 15F, the main body 110 may include one end 1111 of the main surface portion and a second branch portion 1114 protruding from the one end 1111 of the main surface portion as described above with reference to FIG. 15D. The second branch portion 1114 may include the first portion 1112 and the second portion 1113 which are bent, and the second portion 1113 may include the hole 1113H.

The auxiliary shield 60 may be integrally formed with the one end 61 of the main surface portion and may include a protrusion 61W extending in a direction inclined to the one end 61 of the main surface portion. The protrusion 61W may be formed integrally with the one end 61 of the main surface portion and may be placed on a plane different from a plane on which the one end 61 of the main surface portion is placed by an approximately U-shaped incision line CL as illustrated in FIG. 15G. For example, the protrusion 61W may extend as illustrated in FIG. 15E while rotating at a predetermined angle in an RD direction around one edge connected to the one end 61 of the main surface portion.

One end of the auxiliary shield 60 may enter toward a gap between one end 1111 of the main surface portion of the main body 110 and the second branch portion 1114, and the protrusion 61W may be coupled to the hole 1113H of the second portion 1113 of the second branch portion 1114 of the main body 110 as illustrated in FIG. 15F.

As described above, the present disclosure is described with reference to embodiments illustrated in the drawings, and this is only illustrative, and those skilled in the art may understand that various modifications and changes of the embodiments are possible therefrom. Therefore, the true technical scope of the present disclosure should be determined by the technical idea of the appended claims.

DESCRIPTION OF SYMBOLS

1: protector for welding
10: face shield
20, 30, 40, 50, 60: auxiliary shield

What is claimed is:

1. A protector for welding comprising:
    a main body configured to protect a face of a welder, the main body comprising a front portion, an upper portion extending from a top of the front portion and being bent from the front portion, a side portion extending from a side of the front portion and being bent from the front portion, and a bottom portion disposed below the front portion, the upper portion comprising a first rear edge, the side portion comprising a second rear edge, the bottom portion comprising a bottom edge;
    a darkening section located on the front portion of the main body;
    a first auxiliary shield arranged adjacent to the first rear edge of the upper portion of the main body and configured to cover an upper side of a head of the welder, the first auxiliary shield extending in a direction away from the main body, and wherein the first auxiliary shield is linearly movable over the upper portion of the main body; and
    a second auxiliary shield arranged adjacent to the second rear edge of the side portion of the main body and configured to cover an ear of the welder.

2. The protector for welding of claim 1, wherein the first auxiliary shield includes at least one selected from metal or plastic.

3. The protector for welding of claim 1, wherein one of the main body and the first auxiliary shield includes a recess, and the other of the main body and the first auxiliary shield includes a protrusion coupled to the recess, and wherein the recess has a first length which is greater than a first width of the recess and extends in a first direction.

4. The protector for welding of claim 1, wherein the first auxiliary shield is fitted to the upper rear edge of the upper portion of the main body.

5. The protector for welding of claim 1, wherein the first auxiliary shield is configured to move with respect to the upper portion of the main body such that an overlapping area of the first auxiliary shield and the main body is variable.

6. The protector for welding of claim 1, further comprising a third auxiliary shield arranged adjacent to the bottom edge of the bottom portion of the main body and configured to cover a neck of the welder.

7. The protector for welding of claim 1, wherein the bottom portion is inclined inwardly toward the face of the welder with respect to the front portion.

* * * * *